(12) United States Patent
Ye

(10) Patent No.: US 7,147,854 B2
(45) Date of Patent: Dec. 12, 2006

(54) TOPICAL TREATMENT OF PSORIASIS USING NEUTRALIZING ANTIBODIES TO INTERLEUKIN-8

(75) Inventor: George Qing Wei Ye, Mississauga (CA)

(73) Assignee: YES Biotech Laboratories Ltd., Ontario (CA)

( * ) Notice: Subject to any disclaimer, the term of this patent is extended or adjusted under 35 U.S.C. 154(b) by 540 days.

(21) Appl. No.: 10/200,515

(22) Filed: Jul. 23, 2002

(65) Prior Publication Data

US 2003/0147890 A1    Aug. 7, 2003

Related U.S. Application Data

(63) Continuation-in-part of application No. 09/956,968, filed on Sep. 21, 2001, now abandoned, which is a continuation of application No. 09/446,069, filed as application No. PCT/CA98/00604 on Jun. 23, 1998, now abandoned.

(30) Foreign Application Priority Data

Jun. 23, 1997    (CN) ................................ 97 1 12184

(51) Int. Cl.
*A61K 39/395*    (2006.01)
(52) U.S. Cl. .................... 424/145.1; 424/184.1
(58) Field of Classification Search ............. 424/145.1, 424/184.1
See application file for complete search history.

(56) References Cited

U.S. PATENT DOCUMENTS

| 4,816,397 A | 3/1989 | Boss |
| 4,816,567 A | 3/1989 | Cabilly |
| 4,975,369 A | 12/1990 | Beavers |
| 4,978,745 A | 12/1990 | Schoemaker |
| 5,658,570 A * | 8/1997 | Newman et al. .......... 424/184.1 |
| 5,750,105 A | 5/1998 | Newman |
| 6,024,956 A | 2/2000 | Matsushima |

FOREIGN PATENT DOCUMENTS

WO    WO 95/23865    *    9/1995

OTHER PUBLICATIONS

Akita et al. Journal of Food Science, 1992, vol. 57, No. 3, pp. 629-634.*
Merck Index, 1983, 10th ed., p. 1094.*

* cited by examiner

*Primary Examiner*—Christina Chan
*Assistant Examiner*—Yunsoo Kim
(74) *Attorney, Agent, or Firm*—Fei-Fei Chao; Andrews Kurth LLP

(57)    ABSTRACT

The present invention provides a topical preparation for treating patients with skin inflammatory disease. The topical preparation contains an antibody to interleukin-8 (IL-8) and a pharmaceutically acceptable carrier. The antibody can be a monoclonal antibody, a polyclonal antibody, an antibody fragment, or a combination thereof. The monoclonal antibody is a murine anti-human IL-8 monoclonal antibody produced in a hybridoma. The polyclonal antibody is a chicken anti-human polyclonal antibody, which is prepared by immunizing a chicken with human IL-8, collecting eggs from the immunized chicken, and purifying the IgY from the eggs. The topical preparation is effective in topically treating inflammatory skin diseases. The present invention also provides a method for treating patients with skin inflammatory disease, which is by topically applying an effective amount of the topical preparation onto patients with skin inflammatory disease.

10 Claims, 2 Drawing Sheets

TOPICAL TREATMENT OF PSORIASIS USING NEUTRALIZING ANTIBODIES TO INTERLEUKIN-8

RELATED APPLICATIONS

The present invention is a continuation-in-part of U.S. patent application Ser. No. 09/956,968 filed on Sep. 21, 2001, now abandoned which is in turn a continuation of U.S. patent application Ser. No. 09/446,069 filed on May 12, 2000, now abandoned. The abandoned U.S. patent application Ser. No. 09/446,069 is a national stage of PCT International Patent Application PCT/CA98/00604 filed on Jun. 23, 1998, which claims priority of Chinese Patent Application No. CN 97112184.2 filed on Jun. 23, 1997. All the parent applications and the priority applications of the subject application are herein incorporated by reference.

FIELD OF THE INVENTION

The present invention relates to topical preparations for treatment of inflammatory skin diseases. The topical preparations contain an antibody to human interleukin-8 (IL-8). The antibody includes, but are not limited to, monoclonal antibodies, polyclonal antibodies, chimeric antibody, and antibody fragments therein, all having neutralizing activity to IL-8. The preferred topical preparations contain an antibody to IL-8 and a base cream. The base cream facilitates the penetration of antibodies into psoriatic lesions. The topical preparations are particularly effective for treatment of psoriasis and other inflammatory skin diseases such as eczema. The present invention also relates to methods for making the topical preparations and treating patients with skin inflammatory diseases.

BACKGROUND OF THE INVENTION

Psoriasis is a common, noncontagious, chronic, inflammatory disease with unknown cause. The disease creates worldwide health problems. For example, psoriasis affects nearly 3% of the general population in Faroe Islands and Denmark. Over 7 million people in the United States are afflicted with the disease, which represents a 2% of the population.

The most common symptoms of psoriasis include sharply circumscribed salmon pink patches covered with silvery white scales. Diagnosis is usually made by observation and examination of the skin. Different types of psoriasis exist and range from mild to severe. Psoriasis is variable, and one type can change into another type or several types can coexist at the same time. The National Psoriasis Foundation describes the types of psoriasis as follows:

1. Plaque Psoriasis

The major symptoms include raised, inflamed lesions that are covered in white scale. It is among the most common types, which is also called psoriasis vulgaris. Plaque psoriasis can be found anywhere on skin, more often on scalp, elbows, knees, and trunk of the body.

2. Guttafe Psoriasis

The major symptoms include small, drop-like dots with some scale. Guttafe psoriasis can be found on trunk, legs, and arms of the body.

3. Inverse Psoriasis

The major symptoms include smooth inflamed lesions with no scale. Inverse psoriasis can be found at skin folds, armpit, and groin of the body.

4. Erthrodermic Psoriasis

The major symptoms include severe sloughing of the skin with redness. Erthrodermic psoriasis can be found anywhere on body.

5. Psoriatic Arthritis

The major symptoms include swelling and inflammation of joints, which results from 10% of psoriasis patients. Psoriatic arthritis can be found on knees, hips, elbows, spine, hands, and feet of the body.

6. Scalp Psoriasis

Scalp psoriasis is the usual plaque type. Scalp psoriasis exists in 50% of psoriasis patients.

7. Nail Psoriasis

The major symptoms include pitting, discoloration, and loss of fingernails and toenails. Nail psoriasis is usually shown by inflammation of skin around the nail.

A combination of genetic, environmental, and immunological factors may contribute to psoriasis. It is believed that a person is predisposed to developing psoriasis, however, the pattern of inheritance has not been found. Only one in three patients reports a family history of the disease, whereas others show no incidence of psoriasis in the family. Important triggers have been found that may initiate the development of the disease in those that are predisposed to developing the disease. The triggers may include superantigens such as bacteria, virus, and fungus, vaccinations, intramuscular injection, certain drugs, stress, injury to the skin, and Koebner phenomenon. As a result of the trigger, the immune system of the person predisposed to developing the disease causes excessive skin cell reproduction.

In normal skin growth, skin cells produced in the basal cell layer move up through the epidermis to the outermost layer, the stratum corneum. The process from cell birth to cell death takes about 28–30 days. When skin is damaged, the cycle runs much faster. In psoriasis patients, though there is no wound at the site of psoriatic lesions, skin cells called keratinocyte act in a regenerative manner. New skin cells are produced in 2–4 days, thus making it very difficult to shed old cells at an adequate rate. The elevated scaly lesions are a result of the buildup of cells. The white scale is the dead skin cells, and the redness a result of an increase in blood flow to areas of high cell division. Psoriasis is characterized by extreme epidermal hyper-proliferation, which is an excessive growth associated with incomplete and accelerated differentiation and noticeable inflammation of epidermis and dermis at local sites with development of neutrophil microabscess and enhanced induction of cycling T lymphocytes. The cause of psoriasis was initially thought to involve one of the mediators of hyper-proliferation. However, researchers began to focus on the immune system, after by chance it was discovered that cyclosporine with immunosuppressive effects significantly improved conditions in psoriasis patients. Thus, psoriasis is now viewed as an autoimmune disease.

At the present time, there are three major theories relating to the pathogeneisis, origin, and development of psoriasis. The first theory believes that psoriasis is due to T-lymphocytes activated in psoriatic lesions by cytokines that are released from epidermal keratinocyte. The second theory believes that psoriasis derived from antigen dependent T-cell activation which causes the release of cytokines that activate epidermal keratinocyte. The third theory believes that psoriasis is caused by autoimmune reactions of CD8+ "killer" T-lymphocytes with epidermal keratinocyte trigger epidermal activation.

Psoriasis does not affect overall health and is not life threatening, but people do die from complications associated with the disease. The physical and emotional effects of psoriasis can be painful. Psoriasis causes disfigurements which physically limit, thus affect job performance and leisure activities, and cause frustration, embarrassment, fear, and depression for psoriasis sufferers, especially the ones with severe types. Psoriasis is persistent and unpredictable in its course. So far, no single treatment has been found that works for every patient. As a result, a variety of treatments have been developed which can be used alone or in combination to treat the disease. These treatments may diminish symptoms transiently but they are not curative. Very often they are aesthetically unpleasant, expensive, time-consuming, and with side effects. The present treatment is usually disappointing and unsatisfactory.

Mild forms of psoriasis are treated by topical applications of glucocorticoid such as Corticaine. Keratolytic agents, such as sulfur or salicylic acid, are useful adjuvants. Side-effects are mild. Moderate forms of psoriasis are usually treated with anthralin/dithranol or tar preparations such as Pentrax. Side-effects are mild to moderate. Severe cases of psoriasis or mild to moderate forms that do not respond to the conventional therapy may require treatment with systemic medication. Side-effects are usually severe.

Current therapies for psoriasis are as follows:

1. Phototherapy:
   a). Narrow band ultraviolet B phototherapy (UVB) has been used; the side effects include burning and carcinogenesis.
   b). Psoralen with ultraviolet A (PUVA) has been used; there are long term problem of carcinogenesis and short term problems of nausea, phototoxicity, and pruritus.
   c). Photodynamic therapy has been used; the limitations include photosensitivity and tissue destruction.

2. Drugs approved for other uses:
   a). Zidovudine (Retrovir), which is also the drug used to slow AIDS. Side effects involve a decrease in RBC and WBC counts.
   b). Histamine$_2$ Receptor Antagonists has been used for treating psoriasis; the drug is also used to treat stomach ulcers, for example, ranitidine (Zantac) and cimetidine (Tagament) are also used for treating psoriasis. Side effects involve an initially worsening of symptoms.
   c). Antithyroid Thioureylenes is used; the drug is also used for hyperthyroidism. An example is propylthiouracil and methimazole (Tapazole). Side-effects include hypothyroidism, but the side effect is reduced with a topical formulation.
   d). Capsaicin (Zostrix 0.025% cream) is approved for pain relief in rheumatoid arthritis, osteoarthdtis, and neuralgia. The major side effect is stinging.

3. New drugs developed for psoriasis:
   a). Acitretin (Neotegison/Neotigason) is a second-generation monoaromatic retinoid. This drug is teratogenic. Related retinoid Etretinate (Tegison/Tigason) shows similar effects.
   b). Fumaric acid therapy is used. The side effects include abdominal disturbances, lymphopenia, flushing, and mild change of hepatic and renal function. In 85% of patients, long term therapy causes lymphopenia.
   c). Vitamin D derivatives are used. 1,25 dihydroxyvitamin $D_3$ (1,25-(OH)$_2$D$_3$) shows hypercalciuria in systemic and topical applications. A synthetic 1,24-dihydroxyvitamin $D_3$ analogue, Calcipotriene, in the form of ointment (Dovonex ointment), diminishes hypercalciuria side-effects but results in face and intertriginous irritation. Tacalcitol also shows face irritation.
   d). Tazarotene (Tazorac) is an acetylenic retinoid molecule. Topical application showed dose-related irritation.

4. Immune therapy:
   a). Cyclosporine (Sandimmune) is approved for use in organ transplantation. Some side effects are potentially toxic which include headaches, gastrointestinal disturbances, hypertrichosis, paresthesias, and gingival hyperplasia. It is extremely important that nephrotoxicity be carefully monitored with this drug. Side-effects increase with length of time the drug is administered, so it is not an acceptable long-term therapy for patients. A new formulation called Neoral (approved for organ transplantation) may reduce toxicity, but further studies are needed.
   b). DAB$_{389}$1L-2 is a cytotoxin that selectively attacks IL-2 receptors on cells and destroys them. Side effects include: flu-like symptoms, pruritus, and transient transaminase elevation.
   c). Tacrolimus (Prolaf) is a macrolide antibiotic used to treat allograft rejection in liver transplant patients. Side-effects are similar to Cyclosporine.
   d). CTLA41g is an experimental agent that blocks the second signal in T-cell activation. Side-effects are unknown. Clinical trials are in progress.
   e). Anti-CD4 Monoclonal Antibody shows side effects include chills and fever. More in depth toxicity studies are needed.
   f). T-cell receptor peptide vaccines include Vβ3 and Vβ13.1. T-cells are targeted. Clinical trials are in progress to determine toxicity of the therapy.
   g). Other immunologic agents may include TNF-alpha inhibitors and antisense oligonucleotides. Side-effects are unknown.

Monoclonal antibody (mAb) preparations may be effective in fighting malignancy, infection, and immune disorders. A monoclonal antibody is directed against and binds to a single epitope on an antigenic molecule. Characteristics such as homogeneous high binding affinity and specificity make them suitable for developing therapeutics. For example, murine antibodies have been used in diagnosis of human disease, such as leukemias, lymphomas, solid tumors (e.g., colon, breast, hepatic), AIDS and autoimmune diseases. Alternatively, mouse/human chimeric antibodies have been created, and shown to exhibit the binding characteristics of the parental mouse antibody, and effective functions associated with the human constant region. U.S. Pat. Nos. 4,816,567, 4,978,745, 4,975,369, 4,816,397, 5,750,105, and 6,024,956, which are herein incorporated by reference. Generally, the first step for chimeric antibody preparation is isolation of DNA fragments encoding variable heavy and light chains from pre-existing murine hybridoma or spleen cells of immunized mouse. The cloned variable region genes are then ligated into an expression vector containing cloned cassettes of the appropriate heavy or light chain human constant region gene. The chimeric genes are then expressed in a cell line of choice, usually a murine myeloma line.

However, mAb preparations, either as murine monoclonal antibodies or chimeric antibodies, for the most part, have been administered using systemic drug delivery methods, i.e., for internal use. There is hardly any report on the use of mAb in topical treatment.

Topical treatments are preferred for treating psoriasis and other skin inflammatory diseases because there are less side-effects. A concerted effort to develop a topical preparation containing antibodies for treating psoriasis has not been undertaken. This is because it has been accepted that a sufficient level of antibodies cannot be absorbed through the skin to combat psoriasis. It is unknown exactly which biological factors play a role in the manifestation of the disease. This has made it difficult to develop a topical treatment. With a topical treatment, lower levels of antibodies reach the target site. A topical treatment therefore requires the use of an antibody or other active ingredients which neutralize a biological factor which is directly linked to the manifestation of the disease.

The present invention provides an effective topical treatment for skin inflammatory diseases including psoriasis, based on the fact that interleukin-8 (IL-8) or neutrophil-activating protein (NAP-1) has been found to play a significant role in the manifestation of psoriasis and other inflammatory skin conditions. It is not previously known that antibodies or other agents that neutralize IL-8 are effective in the treatment of psoriasis and other inflammatory skin diseases. Particularly, the present invention reveals that the interleukin-8 (IL-8) level is only locally elevated in inflammatory tissues but not in the circulation of the entire body. Expression of high levels of IL-8 in psoriatic tissues contributes to the local inflammation. The topical treatment of cream preparation of present invention has many advantages over systemic administration of anti-IL-8 antibodies. It does not generally affect the levels and expression of IL-8 in the body. Because IL-8 is known to be an important cytokine with multiple physiological functions, total elimination of IL-8 by prolonged treatment of high dose neutralizing antibody in the circulation may cause immune system disturbance and severe side-effects in long term.

The present invention meets the need for a pharmaceutical formulation for topical treatment of psoriasis that is effective in neutralizing biological factors that are directly involved in the manifestation of the disease, and specifically, the need for a topical treatment for psoriasis that contains antibodies for neutralizing IL-8.

The present invention meets the need for a pharmaceutical formulation for protection of antibody activities, and the formulations can keep and maintain the neutralizing activity of antibody for at least two years. The cream formulation of present invention can also facilitate antibodies to penetrate into psoriatic lesions in quantities sufficient to reach therapeutic levels.

The treatment method of the present invention shows advantages over prior treatment methods in the following: (1) the topical application as disclosed in the present invention minimizes the toxic side effects that are often associated with systemic drug delivery, because the treatment is applied locally; (2) the antibodies used in the topical treatment are unique in that they are specific, homogeneous, and can be produced in vitro at infinitum; and (3) the antibodies to IL-8 specifically neutralize IL-8 in psoriatic lesions, but not anything else; and (4) the topical treatment method as disclosed in the present invention does not induce a HAMA reaction that are often associated with systemic delivery of murine antibody, chimeric antibody and humanized antibody.

SUMMARY OF THE INVENTION

The present invention provides topical preparations for treating patients with skin inflammatory disease. The topical preparations of the present invention comprise at least one antibody to human interleukin-8 (IL-8) and a pharmaceutically acceptable carrier for topical treatment of patients with skin inflammatory disease. The antibody used in the topical preparations includes, but is not limited to, monoclonal antibody, polyclonal antibody, antibody fragment, and/or a combination thereof, which has a neutralizing activity against IL-8. The topical preparations containing both a single antibody and a cocktail of several antibodies demonstrate good therapeutic effect on treating patients with skin inflammatory disease, particularly psoriasis and other inflammatory skin diseases such as eczema.

The preferred monoclonal antibody is a murine anti-human IL 8 antibody, which is produced by a hybridoma. Examples of the hybridomas that are capable of producing monoclonal antibodies against human IL-8 include, but are not limited to, IL-8-S2 ("I8-S2"), IL-8-60 ("I8-60"), and IL-8-3C6 ("3C6"), which were deposited on May 14, 1998, at the American Type Culture Collection (ATCC), at 10801 University Boulevard, Manassas, Va. 20110-2209, U.S.A., and given the ATCC Accession No.of CRL-12527 (I8-S2), CRL-12528 (I8-60), and CRL-12529 (3C6), respectively.

The preferred polyclonal antibody of the present invention is a chicken anti-human IL-8 polyclonal antibody, which is prepared by immunizing a chicken with human IL-8, followed by collecting eggs from the immunized chicken, and purifying IgY from the eggs.

The pharmaceutically acceptable carrier for topical treatment includes, but is not limited to, a neutral sterile cream, a base cream, a gel, a jelly, an ointment, an aerosol, a patch, powders, and/or a combination thereof. The preferred pharmaceutically acceptable carrier is a base cream, which contains an emulsifying agent, an oil-phase ingredient, and a water-phase ingredient. The preferred emulsifying agent includes, but is not limited to, fatty alcohol polyoxyethylene ether (Peregal A-20), polyoxylstearate (SG-6), or a combination thereof. The preferred oil-phase ingredient includes, but is not limited to, cetyl alcohol, stearyl alcohol, stearic acid, liquid paraffin, and dimethicone. The preferred water-phase ingredient includes, but is not limited to, glycerol and ethyl paraben. The preferred pharmaceutically acceptable cream formulation can protect and maintain the neutralizing activity of antibodies for at least two years. Preferably, the antibody in the topical preparation constitutes no more than about 100 μg per g, and most favorably 50 μg per g, of the base cream.

The topical preparations are prepared by mixing the anti-human IL-8 antibodies with the pharmaceutically acceptable carrier (such as the base cream) and applied to inflammatory areas of the skin.

The present invention further provides a method for treating patients with skin inflammatory disease. The method contains the step of topically applying an effective amount of the topical preparations of the present invention onto the skin inflammation site of a patient with skin inflammatory disease, such as psoriasis or eczema. The preferred effective amount of the antibody used in the topical preparations is about 0.1–10 μg, most favorably about 1 μg per square centimeter of the inflammatory area daily.

Additionally, the present invention provides a topical preparation which contains at least one antibody to human interleukin-8 (IL-8) which is a chimeric antibody and a pharmaceutically acceptable carrier for topical treatment of patients with skin inflammatory disease. The chimeric antibody does not contain an old World monkey variable region (i.e., the region that binds to said human IL-8). The preferred chimeric antibody contains a murine, most favorably a mouse, variable region that binds to a human IL-8 and a human constant domain. This topical preparation can be used to treat patients with skin inflammatory disease such as psoriasis or eczema.

Finally, the present invention provides a topical preparation which contains at least one antibody to human IL-8 and a base cream. The amount of antibody is preferred no more than about 100 µg per g of the base cream. The topical preparation can be used to treat patients with inflammatory disease (such as psoriasis or eczema) by applying about 0.1–10 µg of antibody per square centimeter of the inflammatory area daily.

DETAILED DESCRIPTION OF THE INVENTION

Figure 1:
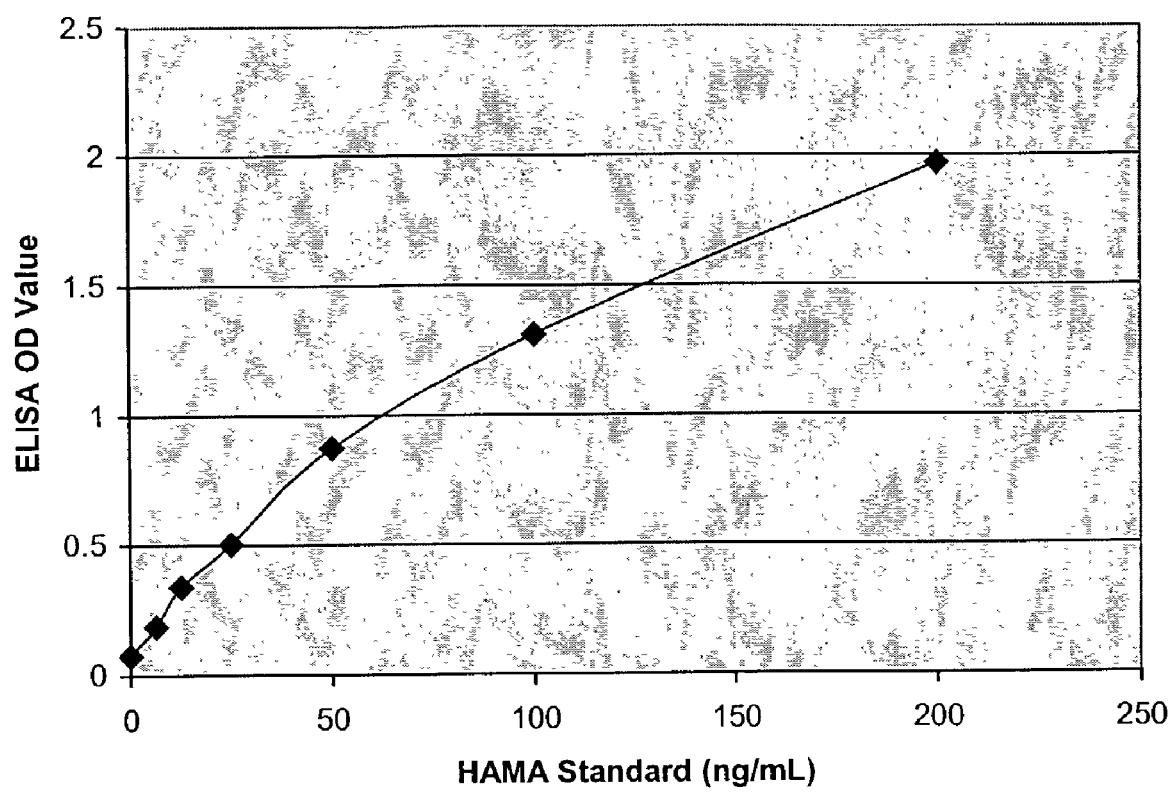
FIG. 1 shows the standard curve for detecting human anti-mouse antibody (HAMA) in serum of patients using ELISA, as described in Example 14 (infra).
Figure 2:
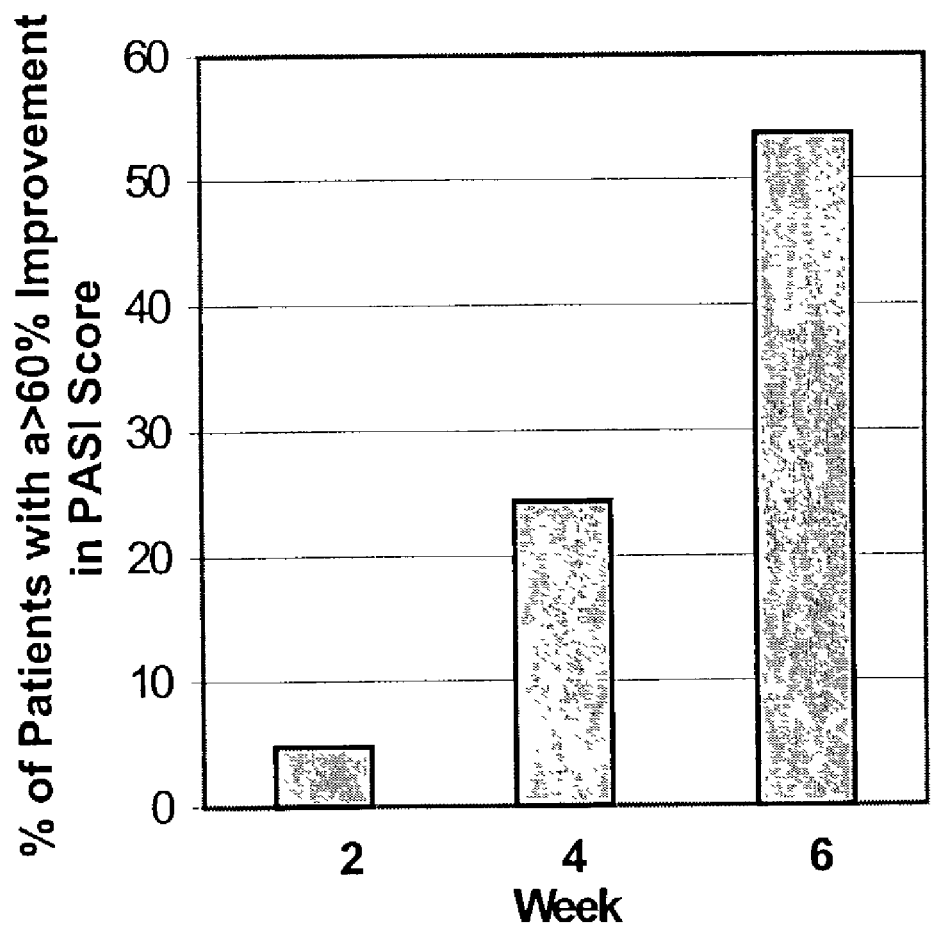
FIG. 2 shows clinical effect on topical treatment of psoriatic patients with the cream of the present invention as described in Example 17 (infra).

The present invention provides a topical preparation for treating patients with skin inflammatory disease. The topical preparation of the present invention contains at least one antibody to human interleukin-8 (IL-8) and a pharmaceutically acceptable carrier for topical treatment on patients with skin inflammatory disease.

Antibody is an immunoglobulin molecule that has a specific amino acid sequence by virtue of which it interacts only with the antigen that induced its synthesis in cells of the lymphoid series (especially plasma cells), or with antigen closely related to it. The term "antibody" as referred herein and also in the claims means a type and/or a kind of antibody. The type of antibody is further defined as a monoclonal antibody, a chimeric antibody, a polyclonal antibody, or an antibody fragment. In the case where the type of antibody is a chimeric antibody, the variable region of the antibody that binds to human IL-8 is not an old World monkey variable region. The preferred chimeric antibody contains a murine immunoglobulin (Ig) variable region which binds to human IL-8 and a human Ig constant domain.

The kind of antibody is further defined as various antibodies within the same type of antibody. For example, there can be various kinds of monoclonal antibodies against human IL-8 (i.e., they can be produced by different hybridomas and/or interacted with different antigenic sites or epitopes). There can also be various polyclonal antibodies (i.e., they can be produced by different animals [e.g., goat anti-human IL-8 polyclonal antibody, rabbit anti-human IL-8 polyclonal antibody, chicken anti-human IL-8 polyclonal antibody]). The topical preparations of the present invention are therapeutically effective using a single type and/or kind of antibody or a combination of several type and/or kind of antibody such as a "cocktail" preparation. The antibody to IL-8 has neutralizing activity on IL-8 upon the topical treatment on the patients with skin inflammatory disease.

When the antibody to IL-8 used is monoclonal antibody, the monoclonal antibody outlined in this invention is obtained through the conventional means. General hybridoma techniques are used and well know, however, in certain cases, specific problems may require some changes and modifications to the known technique. There is no certainty that the required hybridoma can be formed and produce specific antibodies, but the degree of success will depend on the completion of the following steps:

1. Immunization of Mice

Mice are immunized with purified recombinant human interleukin-8 (IL-8, monocyte-derived, 72 a.a. form). The immunization schedule and the IL-8 concentration ("immunogen") should be sufficient to produce satisfactory serum titers of antibodies. Three immunizations with approx. 200 µL of antigen solution every 3–4 weeks by subcutaneous (s.c) and intraperitoneal (i.p.) injections have been found to be effective.

2. Obtaining Spleen Cells from Immunized Mice

Using well-known experimental techniques, the spleen cells of the immunized mice are removed 3–4 days after last ("booster") immunization and suspended in an appropriate medium.

3. Fusion of Spleen Cells with Myeloma

The suspended spleen cells are fused with mouse myeloma cells of a suitable cell line with a suitable fusion promoter, preferably polyethylene glycol (PEG) having a molecular weight from 1000 to 4000. However, other known fusion promoters may be used. Preferably, spleen cells are fused with myeloma cells at a 5:1 ratio.

Any appropriate mouse myeloma cell line may be used for the purpose, but preferably, myeloma cells that do not survive in a selective culture medium containing hypoxanthine, aminopterin, and thymidine (HAT medium) to be used, such as those that lack enzyme hypoxanthine-guanine-phosphoribosyl transferase (HGPRT) or the enzyme thymidine kinase (TK). Especially preferred are myeloma cells and cell lines that do not survive in HAT medium and do not by itself secrete any antibodies. For example, the cell lines of X63-Ag8.653 and Sp2/0-Ag14 are preferred.

After fusion, the cells are cultured in selective HAT medium, which supports the growth of hybridoma cells, but not the growth of unfused myeloma cells. Only fused cells continue to grow, because they have acquired ability to grow in vitro from the myeloma cells, and the ability to survive in selective medium from the spleen cells.

Hybridoma cells must be grown in suitable culture media. For example, RPMI 1640 medium or Dulbecco's Modified Eagle's Medium is used for the culture. The medium is supplemented with 10–15% fetal bovine serum. At the beginning of cell growth, "feeder cells" such as spleen cells, bone marrow, normal mouse peritoneal exudate cells, or "hybridoma growth factors" may be added.

4. Testing of Hybridoma

As soon as the medium has started to turn acidic (yellow) and the cell colonies are visible, a small amount of the cell culture supernatant should be removed to be tested for the presence of desired antibodies, the antibodies to IL-8.

5. Cloning of Selected Hybridoma

Wells that are tested positive for antibody through the screening assay are selected and cloned as soon as possible using well-known experimental techniques. For example, limiting dilution is the easiest method to ensure their monoclonality.

6. Determination of Antibody Isotypes

The monoclonal antibody isotypes are determined using well-known methods, such as "dipstick" assay/dot blot or ELISA.

7. Testing of Antibodies

Antibodies are tested for their ability to specifically neutralize human IL-8 activity. Three hybridoma cell lines that produce murine antibodies with high neutralizing ability are deposited at the ATCC under the Budapest Treaty Deposit Procedure.

Hybridomas IL-8-S2, IL-8-60, and IL-8-3C6 (also known as 3C6 or 257) were deposited on May 14, 1998, at the American Type Culture Collection (ATCC), at 10801 University Boulevard, Manassas, Va. 20110-2209, U.S.A., and given the ATCC Accession Numbers CRL-12527, CRL-12528, and CRL-12529, respectively.

8. Administration of Monoclonal Antibody

Monoclonal antibodies produced by hybridoma cell lines I8-60, I8-S2, and 3C6 bind to different antigenic sites (or epitopes) of IL-8 and can be utilized singly or in a "cocktail" fashion for topical immunotherapy of psoriasis and other inflammatory skin conditions.

9. Maintaining Hybridoma Cells

To ensure a good stock of hybridoma cells and the antibody it secretes, it is necessary to grow up the cells after repeated clonings. This can be done by production of ascites fluid or bulk tissue culture. For ascites production the preferred hybridoma is injected into mice, which will grow and cause ascitic fluid containing mAb to form in the abdominal cavity. After a suitable length of time mouse ascites can be collected using well known experimental techniques and may provide up to 10 mg/ml of antibody. For bulk culture, the hybridoma clones are cultured in vitro in a suitable medium using static cultures, roller cultures or bioreactors. After a suitable length of time the supernatant from a standard flask can be collected and may provide between 10 to 50 μg/ml.

10. Purification of Antibodies

The bulk antibodies should be purified using well-known experimental techniques such as affinity chromatography to remove all major contaminants.

In addition to monoclonal antibodies, a polyclonal antibody may be used quite satisfactorily as an alternative to the monoclonal antibody "cocktail" for immunotherapy of psoriasis and other inflammatory skin conditions. Polyclonal antibody is prepared by the following procedure:

1. Immunization of Chicken

A chicken is immunized by injecting the chicken with purified recombinant human Interleukin-8 using the standard immunization protocols.

2. Collection of Eggs

After the immunization, eggs from the immunized chicken are collected in a suitable period of time.

3. Purification of Polyclonal Antibody

From the collected eggs, the chicken yolk was purified to obtain IgY.

It is suggested to administer topically to patients suffering from psoriasis and other inflammatory skin conditions, a combination of the monoclonal antibody or polyclonal antibody together with a pharmaceutically acceptable carrier. Preliminary clinical trials have demonstrated that such a topical composition is effective in treating skin inflammatory diseases such as psoriasis and eczema.

The topical preparation of the present invention contains a pharmaceutically acceptable carrier which includes, but is not limited to, a neutral sterile cream, a base cream, a gel, a jelly, an ointment, an aerosol, a patch, powders, or a combination thereof. The preferred pharmaceutically acceptable carrier for the topical preparations is a base cream. The preferred pharmaceutically acceptable carrier possesses a protective effect to protect and maintain the neutralizing activity of antibodies in cream for at least two years.

The base cream used in the topical preparation contains an emulsifying agent, an oil-phase ingredient, and a water-phase ingredient.

The preferred emulsifying agent includes, but is not limited to, peregal A-20, softener SG, or a combination thereof.

Peregal A-20 is also known as fatty alcohol polyoxyethylene (20) ether. The chemical formula of Peregal A-20 is $RO(CH_2CH_2O)_{20}H$ which belongs to polyoxyethylene alkyl ethers. Peregal A-20 is a non-ionic surfactant and is frequently used as an oil/water emulsifier. Emulsifying agents with similar characteristics as Peregal A-20 include Brij (trade name), which differs from Peregal A-20 in the degree of polymerization of oxyethylene and thus, differs in physical characteristics. Peregal A-20 is a condensate of fatty alcohol and 15 units of polyoxyethylene. Peregal A-20 alone can not make a good cream base; the combination of Peregal A-20, softener SG, and/or emulsifier SE-10 would make a better cream base.

Softener SG is also called Softener SME-4, or Softener SG-6. The chemical name is polyoxyl(6)stearate. The chemical formula is $C_{30}H_{60}O_6$ with a molecular weight of 548.14. The structural formula is $C_{17}H_{35}COO(CH_2CH_2O)_6$H. Softener SG is a polymer or co-polymer of polyoxyethylene stearate, which is used as non-ionic surfactant for oil/water emulsifier. As an emulsifying agent, the similar type of emulsifying agent includes myri-type emulsifier, which differs from softener SG in the degree of polymerization of oxyethylenes, thus, differs in physical properties.

As for the oil phase ingredient, cetyl alcohol, stearyl alcohol, stearic acid, liquid paraffin, dimethicone, or a combination thereof can be used. Cetyl alcohol has a chemical formula of $C_{16}H_{34}O$ with a molecular weight of 242.44. The structural formula is $CH_3(CH_2)_{14}CH_2OH$. Cetyl alcohol is a solid fatty alcohol. As a co-emulsifying agent and oil phase ingredient, cetyl alcohol improves the texture of the product and increase the adhesives, lubricity, and stability of the emulsifying agent. Cetyl alcohol is especially useful for cream and ointment for which water or aqueous solution needs to be added.

Stearyl alcohol has a chemical formula of $C_{18}H_{38}O$ with average molecular weight of 244–288. The structural formula is $CH_3(CH_2)_{16}CH_2OH$. Stearyl alcohol is a long-chain fatty alcohols. As a co-emulsifying agent and oil phase ingredient, the addition of stearyl alcohol can increase the texture of the product, adhesiveness, lubricity, and stability of the lotion. Thus, stearyl alcohol is especially useful for cream and ointment for which water or aqueous solution needs to be added.

Stearic acid has a chemical formula of $C_{18}H_{36}O_2$. Stearic acid is a long-chain fatty acid. As an oil phase ingredient, stearic acid is emulsified into small droplets. Because of the solidifying property, stearic acid increases the viscosity of the base cream, thus, the viscosity of the base cream can be adjusted according to the formulation and season by adjusting the amount of stearic acid in the composition. Cream based made from stearic acid looks smooth and nice. After being spread onto the skin, water contents evaporate, and thus, leave a layer of membrane formed by stearic acid which provides protection for the skin.

Liquid paraffin is a mixture of liquid saturated alkanes. Liquid paraffin is useful for adjusting the viscosity of the base.

Dimethicone has a chemical name of dimethyl polysiloxane. The structure is as follows:

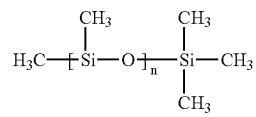

As an oil phase ingredient, dimethicone has function in lubrication, and is easy to apply and spread, non-irritating for skin. Dimethicone is commonly used as lubricant in cream with a maximum amount of 10–30%; dimethicone is also often combined with other oil phase ingredient to make protective ointment.

As for the water phase ingredient, glycerol, ethyl paraben, or a combination thereof can be used.

Ethyl paraben has the chemical name p-hydroxy benzoic acid ethyl ester. Ethyl paraben has a chemical formula of $C_9H_{10}O_3$ with a molecular weight of 166.18. Ethyl paraben belongs to solid fatty alcohols with a chemical structure of

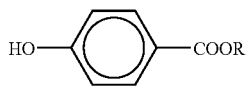

where R=—$CH_2CH_3$

Ethyl paraben is used as preservative. Chemicals with similar characteristics as ethyl paraben include p-hydroxy benzoic acid methyl ester (R=—$CH_3$; Methyl paraben), p-hydroxy benzoic acid propyl ester (R=—$CH_2CH_2CH_3$; Propyl paraben), p-hydroxy benzoic acid butyl ester (R=—$CH_2CH_2CH_2CH_3$; Buthyl parpaben).

Glycerol belongs to triols, and a chemical structure of

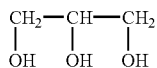

Glycerol is useful as lubricant, humectant, and the concentration used is equal to or lower than 30%. Chemicals with similar characteristics include propylene which belongs to diols and has a chemical structure of:

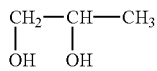

In a preferred embodiment, the base cream of the topical preparation contains a combination of Peregal A-20 and softener SG as the emulsifying agent, a combination of cetyl alcohol, stearyl alcohol, stearic acid, liquid paraffin, and dimethicone as the oil-phase ingredient, and a combination of glycerol and ethyl paraben as the water-phase ingredient.

The anti-IL-8 antibody is probably absorbed into psoriatic lesions in a sufficiently high amount so as to neutralize IL-8 at the epidermal surface for a long period, thus permitting slow penetration of a therapeutically effective dose. Another possible reason for the topical preparations to be effective is that the defective permeability barrier in psoriasis allows greater penetration of the antibodies into the epidermis.

In addition to the antibody and the pharmaceutically acceptable carrier, other neutralizing agents may be introduced in order to produce a more effective cream. The neutralizing agent may be an IL-8 receptor blocking agent, for example a peptide that binds to IL-8 receptor site or antibodies to IL-8 receptor (IL-8R) or soluble IL-8 receptors.

The following example is illustrative, but not limiting the scope of the present invention. Reasonable variations, such as those occur to reasonable artisan, can be made herein without departing from the scope of the present invention.

EXAMPLE 1

Production of Mouse Anti-Human IL-8 Monoclonal Antibodies

The murine anti-human IL-8 monoclonal antibodies used in the topical preparations of the present invention were produced by the following process:

1. Selection of Immunogen

Purified recombinant human interleukin-8 (rhIL-8) derived originally from human monocyte was obtained from Pepro Tech, USA. It consisted of 72 amino acids, had a molecular weight of 8.5 kDa, purity of more than 98% by N-terminal assay, and as shown by SDS-PAGE silver staining, strong chemotactic activity to human neutrophils by chemotaxis assay.

2. Immunization of Mice

Female BALB/c mice from Charles River Laboratories, Inc., Canada, were immunized with rhIL-8. The immunization procedure was as follows:

Antigen 200 μl (20 μg rhIL-8/200 μl PBS) was added with 200 μl Freund's Complete Adjuvant to make a 400 μl antigen emulsified solution.

At day 1, the antigen emulsified solution was injected subcutaneously (s.c.) into mice at multiple sites on back. At day 27, 400 μl antigen solution (20 μg rhIL-8/400 μl PBS) was added with 400 μl Freund's Incomplete Adjuvant, and the mice were immunized by intraperitoneal injection (i.p.). At day 59, the same procedure was conducted on mice as day 27. At day 91, the same procedure was conducted on mice as day 27. At day 152, the mice were immunized by i.p. injection with 20 μg rhIL-8/400 μL PBS antigen solution. At day 155, the spleens of the mice were removed and prepared for cell fusion.

3. Cell Fusion

Murine SP2/0-Ag 14 myeloma cells (ATCC, CRL 1581), which didn't secret heavy or light chain of immunoglobulins, were used. The cell line was resistant to 8-azaguanine and failed to survive in HAT medium. SP2/0-Ag14 was widely used as fusion partner to prepare mAb secreting hybridoma.

SP2/0 Ag14 myeloma cells in logarithmic phase were washed with serum-free RPMI 1640 medium twice. Then, spleen cell suspension prepared under sterile conditions was washed with serum-free RPMI 1640 medium twice. Spleen cells and SP2/0-Ag14 cells were mixed at a 5:1 ratio, then centrifuged at 1500 RPM for 7 minutes and the supernatant was removed.

Slowly, 1 ml of 50% PEG4000 (MW:3000–4000) (GIBCO RL, USA) was added into the pellet, which process took 1 minute. The mixture was let to sit for 1.5 min. Five (5) ml of serum-free RPMI 1640 medium was added slowly into the mixture, which process took 2.5 min. The mixture was let to sit for 5 min. The mixture was then centrifuged at 1000 RPM for 5 minutes and the supernatant was removed. Cells were re-suspended in regular RPMI 1640 medium containing 15% FBS (GIBCO BRL).

The above cell suspension was distributed 100 μl (2 drops) into the each well of plate. Plates were placed in a $CO_2$ incubator (37° C.). HAT culture media was exchanged every 3 days. At day 10, HAT culture media was replaced by HT media.

After 14 days of incubation, supernatant from wells with growing colonies were screened for their binding capacity to IL-8 with ELISA and anti-IL-8 positive clones were selected.

4. Cloning of Hybridoma

In limited dilution method, the diluted cell suspension (3–10 cells/ml) was added 2 drops/well to 96 well plate. The plate was then incubated in a $CO_2$ incubator (37° C.). During the incubation, each well was exchanged with ⅓ fresh culture RPMI 1640 culture media every 3–4 days. Ten (10) days later, the second screen and cloning were carried out. The clones whose mean cloning rate was <66.7 and mean antibody positive rate was 100% were deemed monoclonal after three successive clonings.

Results:

There were 9 clones that were deemed monoclonal specific for human IL-8.

EXAMPLE 2

Characterization of Monoclonal Antibodies

The monoclonal antibodies obtained from Example 1 was further characterized as follows.

1. Immunoglobulin Subtypes

The isotypes of the IL-8 mAbs were identified with the Mouse Ig sub-typing kit (BioRad, USA) according to the instructions.

Results:

The results of the isotypes of the IL-8 mAbs identified are summarized in the following Table 1.

TABLE 1

List of Immunoglobulin Subtypes of Anti-IL-8 mAbs.

| Clone Number | Subclass |
|---|---|
| I8-S1 | IgG2b, kappa |
| I8-S2 | IgG2b, kappa |
| I8-60 | IgG1, kappa |
| I8-61 | IgG1, kappa |
| I8-62 | IgG1, kappa |
| I8-63 | IgG1, kappa |
| I8-64 | IgG1, kappa |
| I8-65 | IgG1, kappa |
| 3C6 | IgG1, kappa |

2. Specificity

All IL-8 mAbs were tested for cross-reaction to various cytokines and chemotactic factors by ELISA. ELISA was conducted according to the conventionally known procedures.

Results:

As shown in Table 2, no cross-reaction with various cytokines, chemotactic factors can be detected by ELISA. The mAbs are specific to IL-8.

EXAMPLE 3

Neutralizine Tests

Three purified anti-IL-8 mAbs, which obtained from hybridoma clone Nos. I8-60, I8-3C6 and I8-S2, and polyclonal antibodies purified from the eggs of the immunized chickens, and antibodies isolated from cream formulation were tested for neutralization effect on IL-8 using a chemotaxis assay as follows:

1. Hybridoma Clones I8-60, I8-S2 and 3C6 and Polyclonal Antibodies to rhIL-8

Human IL-8 (rhIL-8) was incubated with purified IL-8 60, I8-S2 or I8-3C6 monoclonal antibodies and anti IL-8 polyclonal antibodies from eggs of chicken respectively at 37° C. for 30 minutes. The final concentration of the rhIL-8 was 10 ng/ml, an optimal dose of rhIL-8 for eliciting IL-8 RB/293 cell migration response. The mixture of antibody and antigen was individually added into the lower well of the chemotaxis assay chamber while the IL-8 Receptor B/293 cells were in the upper well of the chamber. The upper and lower wells were separated with 5 μm pore-size polycarbonate membrane filter. The chamber was incubated at 37° C. for 5 hours with humidified air 5% $CO_2$. The membrane filter was then stained by Dift-Qick. The inhibition of IL-8 RB/293 cells migration to IL-8 by neutralizing anti IL-8 antibodies was calculated as the formula of following:

$$1 - \frac{(\text{Cells Migration to } IL\text{-}8 + \text{Anti } IL\text{-}8) - (\text{Cells Migration to Medium} + \text{Anti } IL\text{-}8)}{(\text{Cells Migration to } IL\text{-}8 - \text{Cells Migration to Medium})} \times 100\%$$

Results:

1. Monoclonal Antibody Clone I8-60, I8-S2 and 3C6

The clones I8-60, I8-S2 and 3C6 monoclonal antibodies displayed a very high neutralizing activity at Ab:Ag=500:1 and 5000:1 respectively. See Table 3.

TABLE 2

Testing Specificity of mAbs to IL-8

| | Cytokine | | | | | | | |
|---|---|---|---|---|---|---|---|---|
| | Il-8 | GM-CSF | TGF-β | MCAF | TNF-α | IL-7 | IL-16 | IL-1β | bFGF |
| ELISA O.D. | Over | 0.037 | 0.021 | 0.023 | 0.039 | 0.060 | 0.044 | 0.029 | 0.027 |

| | Cytokine | | | | | | | |
|---|---|---|---|---|---|---|---|---|
| | MCP-3 | M-CSF | EGF | GROα | PF-4 | ENA78 | NAP-2 | $GCP_2$ |
| ELISA O.D. | 0.024 | 0.044 | 0.044 | 0.097 | 0.113 | 0.073 | 0.031 | 0.088 |

TABLE 3

Inhibition of IL-8 RB/293 Cells Migration to IL-8
By Neutralizing Anti IL-8 Monoclonal Antibodies

| Clone No. | Ag Conc. (ng/ml) | Ab Conc. (μg/ml) | Average Inhibition Rate (%) | Ab:Ag (w/w) | Ab:Ag (mol./mol.) |
|---|---|---|---|---|---|
| IL-S2 | 10 | 5 | 97.8 | 500 | 28.33 |
| IL-60 | 10 | 5 | 98.4 | 500 | 28.33 |
| 3C6 | 10 | 50 | 95.1 | 5000 | 283.33 |

2. Anti IL-8 Polyclonal Antibodies

The anti IL-8 polyclonal antibodies manifested a very high neutralization activity at Ab:Ag=5000:1. See table 4.

TABLE 4

Inhibition of IL-8 RB/293 Cells Migration to IL-8
By Neutralizing Anti IL-8 Polyclonal Antibodies

| Ag Conc. (ng/ml) | Ab Conc. (μg/ml) | Lot No.: JL0697 | JL2197 | Au2897 | Nv0397 | De0197 | Mixed | Average | Ab:Ag (w/w) | Ab:Ag (mol/mol) |
|---|---|---|---|---|---|---|---|---|---|---|
| 10 | 50 | 94.5 | 95.8 | 96.3 | 93.8 | 93.3 | 105.4 | 96.5 | 5000 | 283.33 |

2. Testing of Neutralizing Activity of Antibodies from Cream Formulation

The mAbs isolated from cream formulation which has been stored for at least two years manifested a very high neutralizing activity at Ab:Ag=450:1. See Table 5:

TABLE 5

Inhibition of IL-8 RB/293 Cells Migration to IL-8
By Neutralizing Anti IL-8 Monoclonal Antibodies
isolated from Cream Formulation

| Ag Conc. (ng/ml) | Ab Conc. (μg/ml) | Lot No.: 990317(2) Exp. I | Exp. II | Average | Ab:Ag (w/w) | Ab:Ag (mol./mol.) |
|---|---|---|---|---|---|---|
| 10 | 4.5 | 106.34 | 96.18 | 101.26 | 450 | 25.5 |

Conclusion:

This result demonstrates that cream formulation of present invention possesses a protective effect to protect and maintain the neutralizing activity of antibody in cream for at least two years.

EXAMPLE 4

Epitope Recognition of Monoclonal Antibodies with Neutralizing Activity

The monoclonal antibodies obtained from hybridomas I8-S2, I8-60 and 3C6 were tested to determine if they recognized the same or different antigenic epitope. The method was described as follows:

Recombinant IL-8 at a concentration of 0.02 μg/ml was coated on a 96-well microplate. ELISA Additivity Test was used. See Friguet, B. et al., J. Immunol. Methods, 60:351–358 (1983). Index (AI)=[(2OD$_{1+2}$)/(OD$_1$+OD$_2$)−1]×100% was determined. Using the method, an AI>50% indicated that the two antibody clones recognized different epitopes. Results in Table 6 indicated that mAbs from hybridomas I8-S2, I8-60, and 3C6 recognized different epitopes on the IL-8 molecule.

TABLE 6

Recognition of Epitopes of IL-8 Molecule by Monoclonal Antibodies.

| Second Reaction Clones | First Reaction Clones | | |
|---|---|---|---|
| | I8-S2 (AI %) | I8-60 (AI %) | 3C6 (AI %) |
| I8-S2 | — | 100.3 | 56.7 |
| I8-60 | 90.6 | — | 108.1 |
| 3C6 | 84.3 | 74.4 | — |

EXAMPLE 5

Bulk Production and Purification of Monoclonal Antibodies with Neutralizing Activity A large quantity of the monoclonal antibodies obtained from hybridomas I8-60, I8-S2, and 3C6 were prepared as the following:

Hybridoma I8-60, I8-S2, or 3C6 were separately transferred to and grown in mice. At day 1, Balb/c mice were injected intraperitoneally with 0.5 ml of Pristane (2,6,10,14-tetramethylpentadecane). At day 7, the hybridoma cells were washed with PBS and 1×10$^6$ cells were injected into each mouse using i.p. route. After two weeks, the ascites fluid was removed from mice by well-known experimental techniques.

Recombinant Protein G Agarose (GIBCO BRL, USA) was used to purify IgG antibody from cell culture supernatant or ascites. Binding Buffer (Sodium Phosphate, pH 7.0/0.15M Sodium Chloride) and Eluting Buffer (0.1 M Glycine Hydrochloride, pH 2.6) were used for purification by protein G affinity chromatography.

For every batch of mAbs purified by protein G affinity chromatography, the specificity and binding affinity were tested by ELISA method. IL-8 was coated at 0.1 μg/well and the mAb titers at their end point were found to be 0.1 ng/ml (I8–60), 0.1 ng–1 ng/ml (I8-S2), and 100 ng/ml (3C6). Purified and quality-controlled mAbs were filtered by 0.22 μm Sterile Millex-GS filter for sterilization (Millipore, Canada), then lyophilized and stored at −20° C.

EXAMPLE 6

Production of Chicken Anti-Human IL-8 Polyclonal Antibodies

Polyclonal antibodies against human IL-8 were prepared as follows:

1. Selection of Immunogen

Purified recombinant human IL-8 was used to immunize chicken for producing polyclonal antibodies.

2. Immunization of Chicken

Shaver Browns laying hen was immunized with the selected recombinant human IL-8. The immunization procedure was as follows:

200 μg IL-8 was dissolved in PBS and emulsified with an equal volume of Complete Freund's Adjuvant. A total of 600 μl mixture solution was injected subcutaneously (s.c) and intramuscularly (i.m.) in various combinations in 4 sites on each breast of the chicken. At days 17, 29, 42, 56, 118, the hen was boosted with 100 μg IL-8 emulsified with an equal volume of Freund's Incomplete Adjuvant. At day 187, the hen was boosted with 200 μg of IL-8 emulsified with an equal volume of Freund's Incomplete Adjuvant. The hen eggs were collected and the egg yolk IgY was purified by Gallus Immunotech, Canada.

3. Testing of Specificity

The polyclonal antibody was tested for the cross-reactivity against human serum albumin and other cytokines by the conventional means. It demonstrated that the polyclonal antibodies exhibited no detectable cross-reactivity with other cytokines and human serum albumin.

4. Testing of Neutralizing Activity

The purified IgY from egg yolks was tested for the neutralizing activity on IL-8 by a chemotaxis assay. The IgY antibody at 50 μg/ml showed 96.5% inhibition to 10 ng/ml IL-8 induced IL-8 RB/293 cell migration.

5. Product Form

The chicken IgY polyclonal antibodies were in phosphate buffered saline (pH 7.3) with no preservatives and stored at −20° C.

Results:

The polyclonal antibodies produced by the method of the present invention, the immunization of hens, exhibited very high neutralizing activity specific to IL-8.

EXAMPLE 7

Topical Preparations

The topical preparations of the present invention contained at least one antibody to human IL-8 and a pharmaceutically acceptable carrier. They were prepared as follows:

1. Preparation of Base Cream

The reagents for preparing the base cream were listed in Table 7, and placed in an open stainless steel tank successively.

TABLE 7

Reagents Used to Make 100 kg Base Cream.

| Contents | Amount (by kg) |
| --- | --- |
| Dimethyl silicon oil | 17 |
| Liquid paraffin | 9 |
| Stearic acid | 7.5 |
| Cetyl alcohol | 1 |
| Stearyl alcohol | 3 |
| Glycerol | 20 |
| Ethylparaben | 0.1 |
| Peregal A-20 | 0.45 |
| Softener SG | 0.85 |
| 0.01 M Phosphate Buffer (pH 7.2) | 41.1 |

The stainless steel tank was placed into a thermostat water bath and heated to 80° C., which took approximately 10 minutes. The liquid was thoroughly mixed. Then, emulsifying and homogenizing equipment was placed into the open stainless steel tank, the mixture was stirred for 20 minutes at 3500 rpm until fully emulsified. The temperature of the thermostat water bath was cooled naturally to room temperature, until the mixture became a semi-solid cream. The mixture was being continually stirred.

2. Preparation of Liquid Antibody Mixture No. 1

MAbs I8-S2, 3C6, and I8-60 were prepared in accordance with Example 5. The lyophilized antibodies were reconstituted with 0.01 M phosphate buffer (pH 7.2) to a concentration of 2 mg/ml. For 1000 gm of base cream, 45 mg of single clone antibody was added. Also, in a cocktail immunotherapy, 15 mg of mAb from hybridoma clone I8-S2, 15 mg of mAb from hybridoma clone 3C6, and 15 mg of mAb from hybridoma clone I8-60 were mixed together.

3. Preparation of Liquid Antibody Mixture No. 2

Chicken polyclonal anti-human IL-8 was prepared in accordance with that of Example 6. For 1000 gm of base cream, 450 mg of polyclonal antibody was required. A higher concentration of polyclonal antibody in the cream was needed for polyclonal preparation, because about less than 10% the specific antibody to IL-8 was contained in the whole IgY.

4. Preparation of Topical Composition (Monoclonal)

While the base cream as prepared in step 1 was being stirred using emulsifying and homogenizing equipment, the liquid antibody mixture no. 1 as prepared in step 2 was added to the base cream while stirring with a pasteur aspirating tube. After the antibody mixture was added, the total mixture was stirred for 10 more minutes to form the topical preparation. The topical composition was packaged and stored at 4° C.

5. Preparation of Topical Composition (Polyclonal)

While the base cream as prepared in step 1 was being stirred using emulsifying and homogenizing equipment, the liquid polyclonal antibody mixture no. 2 as prepared in step 3 was dropped into the stirring base cream by a pasteur aspirating tube. After antibody mixture was added, the total mixture was stirred for 10 more minutes. The topical composition was packaged and stored at 4° C.

EXAMPLE 8

Preliminary Treatment of Human Psoriatic Skin Using Topical Preparation (Monoclonal)

The topical preparation of the present invention was tested on voluntary patients with psoriasis as follows:

1. Materials and Preliminary Clinical Protocol

The topical preparation was prepared according to Example 7 and was applied to 29 voluntary psoriasis patients (23 with plaque psoriasis, 4 with erythrodermic psoriasis, and 2 with arthritic psoriasis). All patients received approximately 0.005 g cream/cm$^2$ of lesion area each time. The cream was applied twice a day for 4 weeks.

2. Evaluation of Therapeutic Effects

The effects of treatment was divided in 4 grades for evaluation. They were cured, obvious effective, effective and non-effect. "Cured" was defined as the patients having the plaque diminished completely and the pruritus disappeared; "obvious effect" was defined as the patients having equal to or more than 60% of the plaque diminished and the pruritus was slighted and softened; "effective" was defined as the patients having 20%~60% of the plaque diminished and the pruritus were slighted and softened; "non-effect" was defined as the patients having less than 20% of the plaque diminished or there was the exacerbation of psoriasis.

Results:

A summary of the effects of the topical composition on the 29 voluntary psoriasis patients from the preliminary trials was shown in the following Table 8.

TABLE 8

Effectiveness of the Topical Treatment (Monoclonal Antibody).

| Type of Patients | Number of Cases | Results |
| --- | --- | --- |
| plaque psoriasis | 23 | 12 effective, 11 non-effective |
| erythrodermic psoriasis | 4 | 4 obvious effect |
| arthritic psoriasis | 2 | 2 obvious effect |
| total | 29 | 12 effective, 6 obvious effect, 11 non-effective |

The topical preparation showed an obvious effect for erythrodermic psoriasis and arthritic psoriasis, and might be effective for plaque psoriasis to some degree. No visible side-effects were observed.

Conclusion:

The topical preparation of the present invention was used in the effective method of treating psoriasis, which was external, convenient, and easy to administer, and showed effectiveness in a short period of time.

EXAMPLE 9

Preliminary Treatment of Human Psoriatic Skin Using Topical Composition (Polyclonal)

The topical preparation of the present invention using polyclonal antibodies was tested on treatment of voluntary patients with psoriasis as follows:

1. Materials and Preliminary Clinical Protocol

The topical composition containing polyclonal antibodies was prepared in accordance with Example 7. The composition was applied to 8 voluntary psoriasis patients (4 plaque, 2 erythrodermic, and 2 arthritic). All patients received approximately 0.005 g cream/cm$^2$ of lesion area. The cream was applied twice a day for 4 weeks.

2. Evaluation of Patients

The effects of treatment was divided in 4 grades for evaluation. They were cured, obvious effective, effective and non-effect. "Cured" was defined as patients having plaque diminished completely and the pruritus disappeared; "obvious effect" was defined as patients having equal to or more than 60% of the plaque diminished and the pruritus was slighted and softened; "effective" was defined as patients having 20%~60% of the plaque diminished and the pruritus was slighted and softened; "non-effect" was defined as patients having less than 20% of the plaque diminished or exacerbation of psoriasis.

Results:

A summary of the effects of the topical composition on the 8 psoriasis patients from the preliminary clinical trials were shown in the following Table 9.

TABLE 9

Effectiveness of the Topical Treatment (Polyclonal Antibody).

| Type of Patients | Number of Cases | Results |
| --- | --- | --- |
| plaque psoriasis | 4 | 2 obvious effective, 2 non-effective |
| erythrodermic psoriasis | 2 | 2 obvious effective |
| arthritic psoriasis | 2 | 2 obvious effective |
| Total | 8 | 6 obvious effective, 2 non-effective |

The topical preparation showed an obvious effect for erythromermic psoriasis and arthritic psoriasis, and might be effective for plaque psoriasis to some degree. No visible side-effects were observed.

Conclusion:

The topical preparation of the present invention was used in the effective method of treating psoriasis, which was external, convenient and easy to administer, and showed effectiveness in a short period of time.

EXAMPLE 10

Treatment of Human Eczemic Skin Using Topical Composition (Polyclonal)

The topical preparation of the present invention using polyclonal antibodies was tested on patients with eczema as follows:

1. Materials and Clinical Protocol

The topical preparation was prepared in accordance with Example 7. The composition was applied to 8 eczema patients. All patients received approximately 0.005 g cream/cm$^2$ on lesion area. The cream was applied twice a day for 4 weeks.

2. Evaluation of Therapeutic Effects

The effects of treatment was divided in 4 grades for evaluation. They were cured, obvious effective, effective and non-effect. "Cured" was defined as patients having eczematous lesion diminished completely and the pruritus disappeared; "obvious effect" was defined as patients having equal to or more than 60% of the eczematous lesion diminished and the pruritus was slighted and softened; "effective" was defined as patients having 20%~60% of the eczematous lesion diminished and the pruritus was slighted and softened; "non-effect" was defined as patients having less than 20% of the eczematous lesion diminished or exacerbation of eczema.

Results:

The topical preparation resulted obvious effect on 5 eczema patients, and 3 patients were non-effective with the treatment. Thus, the topical preparation showed an obvious effect in 63% of eczema patients. No visible side effects were observed.

Conclusion:

This method of treating eczema was external, convenient, and easy to administer. It showed effectiveness in a short period of time.

EXAMPLE 11

Examination of the Presence of Anti-IL-8 Antibodies in Epidermis

The following experiment was conducted to determine whether the anti-IL-8 antibodies were present in the epidermis after the topical preparation was administered to the patient topically.

1. Selection of Patients

To validate the assay, the patient with stable plaque psoriasis was selected.

2. Application of the Topical Preparation and Treatment Regime

The anti-IL-8 monoclonal antibody containing cream of the present invention and the control cream base without the antibody were applied. As an internal control, the topical preparation of the present invention in the form of a cream containing the anti-IL-8 antibodies was applied only on one side of the abdomen (left abdomen), while the cream base without the anti-IL-8 antibodies was applied on the other side (right abdomen) of the patient. The creams were applied once a day followed by a gentle scrub for a two-week treatment.

3. Examination

Biopsy specimens were taken from patients after a two-week course of treatment. Three samples (A1, A2, A3) were taken from the left side, and two samples (B1, B2) were taken from the right side. ABC Kit (source: mouse) from Huamei Bioengineering Co., Cryostat BRIGHT, and Light Microscope from Olympus were used for the examination.

4. Immunoperoxidase Staining of Tissue Sections

As a staining control, slide A3 was not incubated with the secondary antibody Ig G/Bio. A1 and B1 were not stained by hematoxylin. A2, A3, and B2 were stained by hematoxylin. Tissue sections were mounted on slides. The slides were incubated in a 0.25% hydrogen peroxide solution (made up in phosphate buffered saline (PBS)), at room temperature (RT) for 30 minutes and washed 3 times in PBS. The slides were incubated with secondary antibody IgG/Bio (1:200) solution at room temperature for 1 hour, followed by 3 more washes in PBS; the slides were incubated with horseradish peroxidase (HRP/A) at room temperature for 1 hour, followed by 3 more washes in PBS; the slides were then incubated with DAB substrate solution at room temperature for 2–5 minutes, followed by staining with Hematoxylin.

After staining, the cover slips were laid on paper towels and a drop of glue was placed in the middle of the cover slip; the slides were inverted on the cover slips, and then, the slides were left on bench and covered with aluminum foil for 30 minutes to allow the glue to harden. After hardening, the slides were examined under the light microscope and photographed.

Results:

As shown in Table 10, positive staining, in brown color, could be seen in the epidermis of the treated lesions (A1, A2) but not in the epidermis of the untreated lesions (B1, B2). No staining was observed on A3 where the Ig G/Bio was used to incubate with the slide. A2 and B2 showed clear structure of tissue after hematoxylin staining. There was no difference between the hematoxylin-stained A1, B1 a non-hematoxylin-stained A2, B2.

TABLE 10

Results of Immunoperoxidase Staining

|    | Antibody Cream | Control Cream | Ig G/Bio | Hematoxylin | Staining (brown) |
|----|----------------|---------------|----------|-------------|------------------|
| A1 | +              |               | +        |             | +                |
| B1 |                | +             | +        |             | −                |
| A2 | +              |               | +        | +           | +                |
| B2 |                | +             | +        | +           | −                |
| A3 | +              |               |          | +           | −                |

Conclusion:

After the topical application of the topical preparation of the present invention onto the patient, the anti-IL-8 antibodies entered into the psoriasis lesions. The brown color staining was specific to anti-IL-8 antibodies, and the hematoxylin staining did not affect the result in the present assay.

EXAMPLE 12

Examination of the Presence of Anti-IL-8 Antibodies in Epidermis After Treatment with the Cream of the Present Invention The following experiment was conducted to identify whether there were anti IL-8 antibodies in the psoriatic lesions after the topical treatment of the anti-IL-8 antibody-containing cream of the present invention.

1. Selection of Patients

Ten patients were selected from Peking Union Medical University Hospital. Five of the patients were male and five were females. In addition, an untreated patient was selected as a negative control. The distribution of biopsy areas was as follows: five from an upper limb, four from the abdomen and one from a lower limb.

2. Treatment Regime

The patients were treated with (1) the anti-IL-8 monoclonal antibody cream of the present invention and (2) the control cream base without the antibody. The patients were treated for 2 weeks.

3. Examination of Patients

Biopsies were obtained from the treated psoriatic skin lesions on patients during the two weeks of treatment. The distribution of biopsy areas was as follows: five from the upper limb, four from the abdomen, and one from the lower limb.

4. Immunoperoxidase Staining of the Tissue

ABC Kit (source: mouse) from LAB VISION, USA and light microscope from Olympus were used for the staining and examination. The Immunoperoxidase staining of tissue sections was conducted as follows:

The eleven paraffin-embedded skin specimens were all sectioned, mounted on slides and stained using the following protocol:

Slides were incubated in a 0.25% hydrogen peroxide solution (made up in phosphate buffered saline (PBS)), at room temperature (RT) for 30 minutes, and washed three times (3×) in PBS. Slides were then incubated with an anti-mouse secondary antibody (Ig/Bio), diluted 1:200 in PBS, at RT for one hour, followed by three washes (3×) in PBS. Slides were then incubated with a horseradish peroxidase (HRP/A) at RT for one hour and washed three times (3×) in PBS. Slides were then incubated with DAB substrate solution at RT for 2–5 minutes. After the reaction was stopped, the slides were stained with Hematoxylin. A cover slip was then glued onto each slide. After drying, the slides were examined under a light microscope and photographed.

Results:

There was no staining on the negative control. Seven of the ten samples had staining distributed as follows: They all had staining in the parakeratotic layer of epidermis and one had additional staining of interstitial cell in the spinum layer. Three samples had no staining. This study showed that anti-IL-8 antibodies have entered the epidermis. The lack of staining in the deeper epidermis could be attributed to either lack of antibody penetration or to low level penetration that was undetected by our assay.

EXAMPLE 13

Testing of Skin Irritation and Sensitization After Applying the Topical Preparation of the Present Invention The topical preparation of the present invention was evaluated for adverse effects, including skin irritation and sensitization.

1. Selection of Patients

Thirty-two (32) patients were tested and evaluated for adverse effects after the anti-IL-8-containing cream of the present invention had been applied to their skin.

2. Treatment Regime

The patients were randomly divided into 4 groups. Each group contained 4 males and 4 females. The test was conducted by applying Finn test patches to the inner sides of the bilateral forearms of the patients for a period of 24 hours.

Each patient was given 12 patches, 6 on each arm including:

a. 4 patches with anti-IL-8 antibody containing cream,
b. 4 patches with base cream only, and
c. 4 blank patches.

With regard to (a), each of the tested group was tested with a different antibody concentration, i.e., the first group (11.25 μg/gram base cream); the second group (22.5 μg/gram base cream); the third group (45 μg/gram base cream); and the fourth group (90 μg/gram base cream). The groups were tested sequentially, i.e., the first group was tested with the lowest dosage, with the last group tested with the highest dosage, and the test for the second group was conducted after the test of the first group was completed.

3. Examination of the Patients

All patches were removed after 24 hours, and the dermal reactions were examined at 0, 24, 48 and 72 hours after patch removal. In addition, the patients were examined for any reactions 7 days after the removal of the patches.

4. Scoring and Recording of the Results

The patients were evaluated and scored for both dermal response and symptoms as follows:

--- a. Scoring for Dermal Response:

0 = No evidence of irritation.
0.5 = Minimal erythema, barely perceptible.
1 = Erythema, readily visible.
2 = Definite erythema, edema.
3 = Erythema, edema, papules and vesicles.
4 = Severe erythema, edema, papules, large vesicles, even necrosis.

b. Scoring for symptoms:

0 = No symptom.
1 = Slight itch and felling hot.
2 = Definite itch and burning.
3 = Severe itch and burning.

---

The observation and scoring were carried out in a double-blind method. For each patient, a total irritation score was calculated by adding up the individual irritation scores from sites a, b, and c on one forearm. The total symptom score was also calculated for each patient. The mean cumulative irritation score for each test group (the total scores of 4 sites from 8 patients in each group divided by 32) and the mean cumulative irritation score of all 128 sites applied with patches, including the patches with base cream only or the blank patches, were all calculated.

Results:

The results were summarized in the following Table 11.

TABLE 11

Scoring of Dermal Response and Symptoms of Treated Patients.

| Dose | Number of Patients | Dermal Response | Symptoms |
| --- | --- | --- | --- |
| 11.2 μg Ab/gm | 32 | 0/32 | 0/32 |
| 22.5 μg Ab/gm | 32 | 0/32 | 0/32 |
| 45 μg Ab/gm | 32 | 1/32 with barely perceptible irritation. | 1/32 felt slight itch. |
| 90 μg Ab/gm | 32 | 1/32 with readily visible erythema | 1/32 felt slight itch. |

As shown in Table 11, the exposure to the anti-IL-8 antibody containing cream of the present invention resulted in minimal skin irritation in the patients.

Conclusion:

The topical preparation of the present invention was safe, and did not cause skin irritation and other noticeable symptoms.

EXAMPLE 14

Detection of Human Anti-Mouse Antibodies in Psoriasis Patients After Six Weeks Treatment with Cream Preparation of Present Invention The topical preparation of the present invention was tested for human anti-mouse antibodies (HAMA) in patients after being treated with the murine anti-IL-8 antibody-containing composition. The development of the HAMA could reduce the effectiveness of the topical treatment. Further, the HAMA response could result in significant toxicity by the formation of immune complex during the subsequent administration of the topical preparation.

Method:

1. Selection of the Patients

Forty-six psoriasis patients were selected for the examination. These patients had been previously treated with the topical preparation of the present invention for 6 weeks.

2. Sampling of the Patients

Serum samples from the patients were obtained and tested for HAMA reaction.

3. HAMA Determination by ELISA

ELISA assay was used to detect the amount of HAMA in serum. Using the following HAMA ELISA kit and protocol, the test achieved a sensitivity of 2–4 ng/ml.

a. The Specimen and Reagents in HAMA Testing Kit.

(1). HAMA testing plate (96-well plate coated with mouse Ig G)
(2). Biotin-Mouse Ig G conjugate.
(3). Avidin-HRP conjugate.
(4). HAMA Testing Standard (goat anti-mouse Ig G antibodies)

(5). Diluent for HAMA Testing Standard.
(6). Wash buffer.
(7). Substrate A.
(8). Substrate B.
(9). Stop Solution.

b. Standards for HAMA testing

The HAMA Testing Standard was dissolved in distilled water and diluted to the concentrations of 400 ng/ml, 200 ng/ml, 100 ng/ml, 50 ng/ml, 25 ng/ml, 12.5 ng/ml, 6.25 ng/ml and 0 ng/ml.

c. ELISA Operation Protocol (Each Sample was Tested in Duplicate)
(1). 50 μl of biotin-mouse Ig G conjugate was put into each well.
(2). 100 μl aliquot of either an HAMA Testing Standard dilution or a serum sample from a patient was introduced into each relevant well.
(3). Each plate was covered, mixed gently by hand, and incubated for 2 hours at 37° C.
(4). After incubation, plates were emptied by inversion and washed 5 times with the wash buffer. After the final wash, the plates were aspirated to dryness.
(5). A 100 μl Avidin-HRP conjugate solution was introduced into each well, and the plate was incubated for 1 hour at 37° C.
(6). After incubation, plates were emptied by inversion and washed 5 times with the wash buffer. After the final wash, plates were aspirated to dryness.
(7). A 100 μl aliquot of a Substrate A and B mixture was added to each well, and the plate was incubated for 10 minutes at 37° C.
(8). A 100 μl aliquot of Stop Solution was added into each well for stopping the reaction.
(9). Absorbance at 450 nm was read with a microwell reader within 30 minutes of previous step.

d. Calculations and Interpretations
(1). The net absorbance was calculated by subtracting the average "0 ng/ml" Testing Standard absorbance from the average obtained for each duplicate sample.
(2). The standard curve was obtained by plotting absorbance (Y-axis) versus concentration of standard (X-axis) on a graph paper.
(3). The concentration of HAMA in each patient sample was determined on the basis of net sample absorbance by reading the corresponding ng/ml concentration from the Standard Curve.

Results:

The data for drawing a HAMA testing standard curve was shown in Table 12.

TABLE 12

HAMA Testing Standard Curve

| | HAMA Standard (ng/ml) | | | | | | |
|---|---|---|---|---|---|---|---|
| | 0 | 6.25 | 12.5 | 25 | 50 | 100 | 200 |
| ELISA O.D. | 0.074 | 0.188 | 0.340 | 0.503 | 0.873 | 1.309 | 1.969 |

The standard curve for HAMA testing was shown in FIG. 1.

Results:

All the forty-six patients showed 0 ng/ml HAMA, thus, no HAMA reaction was detected in the patients treated with topical preparation of present invention.

The absence of HAMA could be explained in two ways. First, since the antibodies administered were interacting locally with over-expressed IL-8 in psoriatic skin, the dosage of anti-IL-8 antibody required for a therapeutic effect was very low. For example, an antibody concentration of only 15 μg/gm was sufficient to generate an "effective" rate of 81.8%. In contrast, systemic treatments with antibodies required an injection of at least a hundred milligrams antibody per dose.

Another reason for the low HAMA response after the treatment was an inherent property of the cream formulation used which allowed a slow penetration of antibodies into the skin. Those antibodies bound and formed a complex with the over-expressed IL-8 locally, and were then promptly removed by the reticuloendothelial system. By not presenting an initial stimuli, we believe, antibodies that penetrated slowly into the skin might be able to evade the host immune response.

Conclusion:

The topical preparation of the present invention, which contained murine antibodies, did not induce detectable HAMA response in the patients after the topical treatment.

EXAMPLE 15

Preliminary Clinical Trial of the Topical Preparation Containing a Single Clone I8-60 Monoclonal Antibody The topical preparation of the present invention containing monoclonal antibodies from the single hybridoma cell line I8-60 was tested for the therapeutic efficacy on patients with skin inflammatory disease. The following clinical study was also carried out with the aim of evaluating the effectiveness of a low-dose (only 15 μg anti-IL-8 mAb/gm) monoclonal antibodies preparation.

Method:

1. Selection of the Patients
a. The Inclusion Criteria
(1). The patients were diagnosed with psoriasis, either as outpatients or inpatients.
(2). The patients whose skin lesion area was less then 20% of whole body area.
(3). The patients could be either male or female.
(4). The patients must not have received any systemic corticosteroid or immunosuppressive agent treatment within the 4 weeks immediately preceding the study.
(5). The patients must not have received any systemic anti-psoriatic treatment within the 2 months immediately preceding the study.
(6). The patients must not have received any topical anti-psoriatic treatment within the immediate 2 weeks preceding the study.
(7). The patients must have consented to take part in the clinical trial.

b. The Exclusion Criteria
(1). The patients who had history of allergic reactions to systemic or topical drugs were excluded.
(2). The patients who had manifestation of systemic infection or clinical evidence for skin eruption accompanied by bacteria or fungus infection were excluded.
(3). The patients who had apparent mental illness, endocrine disease, blood disease, liver disease, kidney disease, heart disease, brain disease, and immuno-suppressive disease were excluded.

(4). The pregnant women, or women planning for pregnancy, and breast-feeding mothers were excluded.

(5). The patients using other drugs such as Lithium, β receptor blocker etc. which might affect the normal course of psoriasis were excluded.

(6). Cancer patients or patients with a history of cancer were excluded.

c. Statistics of the Selected Patients

Eleven psoriasis patients were selected including 7 males and 4 females. The patients' age ranged between 21 and 55 years old. The average age was 33.9 years old. The average course of psoriasis was 7.73±6.4 years old; average course of this time 9.3±7.5 months. All cases were of small plaques and in progressing stage. Two cases had family history of psoriasis. Target lesion distribution of the patients were, upper limbs: 3 cases; thighs: 2 cases; backs: 5 cases; abdomen: 1 case.

2. Treatment Regime of the Patients

The dosage of the treatment was 15 μg Clone I8-60 mAb/gram cream base (15 μg/g). The anti-IL-8 cream Lot number was 200010. The treatment method was an open clinical trial.

3. Criteria of Effectiveness a. Index of Improvement

Using a 0–4 point scale, patients were assigned a score number as defined in Table 13, both before and after the treatment. The effectiveness of the treatment was evaluated by an "Index of Improvement" calculated as follows:

(3) Effective: the patients had target skin lesions partly disappeared; itch and other objective symptoms partly disappeared; index of improvement 30%~59%.

(4) No effect: the patients had target skin lesions almost continued, or no change, or devastated; itch and other objective symptoms had no change or devastated; index of improvement <30%.

Results:

The results were shown in Table 14.

TABLE 14

Results of patients after treatment.

| Name | Gender | Age | Improvement % | Clinical Effectiveness |
|---|---|---|---|---|
| Tan | F | 36 | 90.1% | basically cured |
| Tang | M | 33 | 14.2% | no effect |
| Liu | M | 27 | 40% | effective |
| Zhao | M | 27 | N/A | devastated |
| Zhang | M | 55 | 28.6% | effective |
| Wang | F | 28 | 40% | effective |
| Ding | F | 24 | 50% | effective |
| Guo | M | 52 | 68.4% | obviously effective |
| Pang | M | 31 | 46% | effective |
| Wang | M | 39 | 38% | effective |
| Ni | F | 21 | 91.5% | basically cured |

TABLE 13

Scoring of Treatment Effects.

$$\text{Index of improvement \%} = \frac{\text{(Points before treatment} - \text{Points after treatment)}}{\text{Points before treatment}} \times 100\%$$

| Points | Area of Lesion | Redness of Plaque | Hypertrophic Infiltration | Scale | Itch |
|---|---|---|---|---|---|
| 0 | None | None | None | None | None |
| 1 | 1–4 cm² | Mild | Mild Infiltration, above skin | Little | Mild, scratch less than 3 times/day |
| 2 | 4.1–9 cm² | Middle red | Middle Infiltration, above skin | Mild | Middle, scratch between 4 and 6 times/day |
| 3 | 9.1–16 cm² | Apparent Red | Apparent Infiltration above skin | Apparent | Apparent, scratch between 7 and 10 times/day |
| 4 | 16.1–25 cm² | Black Red | Hypertrophic | Very much | Serious, Lasing. | b. Improvement of Symptoms

According to the improvement of symptoms, criteria of clinical effectiveness were divided into 4 levels as defined below:

(1) Basically cured: the patients had target skin lesions almost disappeared; itch and other objective symptoms disappeared; index of improvement >90%.

(2) Obviously effective: the patients had target skin lesions mostly disappeared; itch and other objective symptoms apparently attenuated; index of improvement 60%~90%.

The clinical effects of the topical preparation of the present invention on the 11 patients were summarized as: 2 cases were basically cured; 1 case was obviously effective; 6 cases were effective; 2 cases showed no effect; no side effects were detected.

$$\text{The Effective Rate} = \frac{\text{(basically cured + obviously effective + effective)}}{\text{number of total cases}} \times 100\% = 81.8\%$$

Finally, this trial using low dose (15 μg/g) of single clone mAb showed a similar effective rate (81.8%) as the treatment using high dose (45 μg/g) of three clones mAbs (effective rate 88.8%).

Conclusion:

The topical preparation of the present invention for treatment of psoriasis was effective with both preparations of a single clone mAb and a "cocktail" of several antibodies.

EXAMPLE 16

Stability of Anti-Human IL-8 Monoclonal Antibody in Cream Formulation

The stability of the anti-human IL-8 monoclonal antibodies from six different lots (lot 20010303, 20010304, 20010305, 20010306, 20010307 and 20010308) of the cream formulation was tested as follows:

Method:

1. Isolation of Antibody from Cream Formulation

The antibodies were isolated from the cream formulation as follows:

Two grams of cream were thoroughly mixed with 10 ml PBS-T solution. This mixture was centrifuged at 15,000 rpm for 15 minutes for twice, and the supernatant was collected for testing.

2. Measurement of Antibody Titer

The antibody titer was determined as follows:

a. Preparation of the Antigen Coated Plate

Purified recombinant human IL-8 antigen was dissolved in 0.05 M carbonate buffer at pH9.5 to get a final concentration of 1 μg/ml. The wells of plate were coated with 100 μl antigen per well and kept at 4° C. overnight. The plate was blocked with 200 μl PBS per well (PBS containing 1% fish gelatin, 5% sucrose) and kept at 37° C. for 2 hours.

b. Standardized Anti-IL-8 mAb

The standardized anti-IL8 mAb (Standards) were diluted in a solution containing 50% inactive calf serum, 40% glycerol, and 10% PBS to reach a final mAb concentration of 10 μg/ml. The Standards were divided into bulk quantities and stored at −70° C.

c. Drawing Standard Curve

The standardized anti-IL8 mAb (Standards) were prepared in the concentrations of 25 ng/ml, 12.5 ng/ml, 6.25 ng/ml, 3.12 ng/ml and 1.56 ng/ml. For drawing a Standard Curve the O.D. value of each Standard sample was determined by an ELISA mathod. The X-axis represented the concentrations of Standard samples, and Y-axis represented the corresponding O.D. values. Table 15 is an example data of Standard Curve:

TABLE 15

OD and mAb Concentration for Standard Curve.

| | Concentration (ng/ml) | | | | | |
|---|---|---|---|---|---|---|
| | 25 | 12.5 | 6.25 | 3.12 | 1.56 | 0 |
| OD 450 value | 1.720 | 0.882 | 0.485 | 0.286 | 0.176 | 0.000 |

For example, a sample with a ½₀₀₀ dilution of cream supernatant showed an $OD_{450}$ 1.208. According to Standard Curve the antibody concentration of this sample is 17.26 ng/ml, and the antibody titer was calculated by 17.26 ng/ml×2000=34.52 μg/g.

3. Long-Term Stability Test

Samples were randomly selected from each lot, and analyzed at the following time-points: every month for the first three months and every three months thereafter. This stability tests had been continued for a period of 12 months and the results are shown in Table 16.

TABLE 16

Antibody Titers at Different Months.

| | Antibody titers at different months (μg/g) | | | | | |
|---|---|---|---|---|---|---|
| Months | 20010303 | 20010304 | 20010305 | 20010306 | 20010307 | 20010308 |
| 0 | 34.1 | 38.2 | 31.9 | 31.0 | 32.8 | 31.5 |
| % of remaining activity | 100% | 100% | 100% | 100% | 100% | 100% |
| 1 | 35.3 | 34.4 | 33.7 | 37.3 | 37.3 | 34.0 |
| % of remaining activity | 103.5% | 90.1% | 105.6% | 120.3% | 113.7% | 107.9% |
| 2 | 35.4 | 33.1 | 31.3 | 33.0 | 32.6 | 32.3 |
| % of remaining activity | 103.8% | 86.6% | 98.1% | 106.5% | 99.4% | 102.5% |
| 3 | 34.8 | 35.4 | 34.5 | 36.1 | 37.4 | 34.3 |
| % of remaining activity | 102.0% | 92.7% | 108.2% | 116.5% | 114.0% | 108.9% |
| 6 | 39.7 | 35.9 | 37.8 | 31.9 | 33.4 | 34.1 |
| % of remaining activity | 116.4% | 94.0% | 118.5% | 102.9% | 101.8% | 103.8% |
| 9 | 29.4 | 28.2 | 29.6 | 26.4 | 30.7 | 31.2 |
| % of remaining activity | 86.2% | 73.8% | 92.8% | 85.2% | 93.6% | 99.0% |
| 12 | 38.6 | 31.4 | 35.6 | 31.8 | 36.1 | 33.0 |
| % of remaining activity | 113.2% | 82.2% | 111.6% | 102.6% | 110.0% | 104.8% |

Results:

The activities of anti-human IL8 monoclonal antibodies from six different lots of cream formulation are very stable for at least 12 months. It meets with the QC criteria as by National Institute for the Control of Pharmaceutical & Biological Products of China.

4. Accelerated Stability Test

The cream samples from the same six lots as shown above were stored at 37° C. and the activities of antibodies have been periodically tested. At each indicated time-point, three samples from each lot were taken out and analyzed. Data from all assays were statistically averaged and summarized in Table 17 (Antibody titer unit: µg/g):

TABLE 17

Data from the Accelerated Stability Test.

| | Days | | | | | | | | | |
|---|---|---|---|---|---|---|---|---|---|---|
| | 0 | 1 | 3 | 5 | 8 | 10 | 13 | 15 | 18 | 20 |
| Titer | 33.42 | 33.50 | 32.34 | 30.85 | 27.39 | 25.67 | 23.36 | 21.88 | 19.24 | 18.62 |
| Percentage | 100% | 102% | 96.7% | 92.3% | 81.9% | 76.8% | 69.9% | 65.5% | 57.6% | 55.7% |

Conclusion:

The above data showed that the antibody titer changed gradually in twenty day period at 37° C., it indicates that the cream formulation demonstrates a protective effect on the antibody activity. It is concluded that antibody stability in cream formulation of present invention is longly maintained.

EXAMPLE 17

Phase II and III Clinical Trials for the Treatment of Psoriasis Vulgaris with Anti-Human Interleukin-8 Monoclonal Antibody Cream Formulation in China The therapeutic efficacy of the topical preparation containing anti-human interleukin-8 monoclonal antibody was investigated on patients with psoriasis vulgaris as in phase II and phase III clinical trials in China.

Example 17.1. Phase II Clinical Trial.

1. Introduction:

In the pathogenesis of psoriasis, IL-8 plays a very strong role in the leukocyte chemotaxis and in the mitogenesis of keratinocyte. IL-8 also plays a key role as mediator in the infiltration of T-lymphocytes and neutrophils into epidermis. Large amounts of IL-8 are found in the psoriatic plaque lesions of skin, contrasting to the unaffected or normal skin where IL-8 is hardly found. Based on this fact, the topical preparations containing anti-human IL-8 monoclonal antibody (45 µg mAb/g cream) for the topical treatment of patients with psoriasis vulgaris has been investgated.

2. Aim

In phase II clinical trial of the topical preparation of present invention, the indications, therapeutic effectiveness and drug safety were closely observed on the patients with psoriasis vulgaris.

3. Clinical Trial Design

Multi-center, randomly double-blind, and parallel contrast method were applied in the phase II clinical trial.

3.1 Indications

The indications were localized plaque psoriasis vulgaris in the progressive stage.

3.2 Choice of Cases

The selected patients were mainly having psoriasis vulgaris in the progressive stage. One hundred cases were selected for the treatment group with topical preparation of the present invention; another one hundred patients were selected for the contrast group administering with base cream (as contrast drug) respectively. The total cases in phase II clinical trial were about 200.

3.3 Diagnostic Standards

The patients were diagnosed according to the typical characteristics of psoriasis vulgaris, expressed as reddish brown clearly demarcated plaques with infiltration, superficial covering of multi-layers of dry, silvery white scales, thin membrane phenomenon on light scratching, petechia on repeated scratching (Auspitz phenomenon). The diagnosis was based on the section of Detailed and Differential Diagnosis, *Clinical Dermatology*, pp 667–669, 2nd ed., chiefly edited by Zhao Bean, Jiangsu Publish House, China (1989).

3.4 Criteria of Selection a. Both hospitalized patients and outpatients were selected.
b. Patients having area of skin lesion less than 20% of the total body surface area (one palm area is approximately equivalent to 1% of one's own body surface area) were selected.
c. Patients having ages of 18–65, male or female, were selected.
d. Patients having progressive stage within two months and resting stage within one year were selected.
e. Patients having no systemic immunological treatment such as corticosteroid or immunosuppressive drugs within the past four weeks and no systemic anti-psoriasis treatment within the past month were selected.
f. Patients having no topical anti-psoriasis treatment of any standard within two weeks were selected.
g. "Letter of Consent" was signed with the agreement of the patient.
h. To minimize the effect of self-curing tendency of the disease, treatment and follow up were carried out in autumn, winter and spring.

3.5 Criteria of Exclusion

Patients were excluded if they had history of allergy to the drug, either systemically or through local contact. Patients having infection manifested either by systemic clinical symptoms or local rash with complications of bacterial or fungal infection were not selected. Patients with obvious endocrinological diseases were not selected. Patients with mental illness were not selected. Patients having hematological diseases, Liver or kidney diseases, Cerebral or cardiovascular diseases were not selected. Patients having hypoimmunological function were not selected. Pregnant women, women planning for pregnancy, and breast-feeding women were not selected. Patients simultaneously using other medications, such as lithium preparations, β-receptor blocker, etc. which may affect psoriasis, were not selected. Patients having cancer or history of cancer were also excluded.

3.6 Criteria of Elimination a. Failure to meet the criteria of selection discovered only during trial.
b. Failure to closely cooperate during the trial or failure to take the medication in proper time or finish the therapeutic course as requested.
c. No side effects were noted but the trial was stopped due to other reasons. For example, the combined use of other drugs that might affect the trial, pregnancy during trial, loss of follow-up, patient request of withdrawal from trial, other complications, and death.
d. Trial had to be stopped due to serious side effects, and immediate and necessary measures must be taken at the same time for the safety of the recipient. This kind of reaction was to be reported within 24 hours to provincial Drug Control and Management Department, State Bureau of Drug Control and Management, organizations which investigated and produced the drug, and the team leader organization. This kind of condition had to be counted and listed in "adverse side effect" category, and was not to be listed in therapeutic effect category.
e. Patients withdrawn from the trial due to adverse side effect of the drug were to be followed up for one week, so as to make definite the final outcome. All clinical materials including a name list of all the patients withdrawn from the trial and the reasons for their withdrawal could be provided.

3.7 Administration

The topical preparation (both for the treatment group and the contrast drug group) was applied to patients with approximately 0.005 g cream/cm² of lesion area twice daily for six continuous weeks topically.

3.8 Index and Method of Observation

Patients were observed once every week both before and after treatment. Cured patients were followed up for four weeks after stopping treatment to observe any possible recurrence. Detailed and accurate records were kept by collecting the following information at each weekly follow-up including the change of conditions such as red plaques of skin lesion, infiltration hypertrophy, and degree of scaling. Symptoms and self-feeling should also be recorded. Degree of severity was scored as 0, 1, 2, 3, 4.

Each patient in the trial group and the control group had routine blood and urine examination, liver and kidney function test (ALT, BUN), and E.K.G. before and after the treatment. Each center provided pictures for five typical cases before and after treatment.

3.9 Criteria for Judgment of Therapeutic Effect

Clinical therapeutic effect was divided into four categories according to the degree of improvement of symptoms and therapeutic index. The four categories were defined as: basically cured, obviously effective, improved, and no effect.

$$\text{Degree of improvement (Therapeutic index) \%} = \frac{\text{Score (before treatment)} - \text{Score (after treatment)}}{\text{Score before treatment}} \times 100\%$$

Basically cured was defined as the patients having skin rash basically subsided, symptoms (abnormal self-feeling) such as itchy feeling disappeared, and showed degree of improvement (index of therapeutic effect) $\geq 90\%$.

Obviously effective was defined as the patients having skin rash obviously subsided, symptoms such as itchy feeling obviously alleviated, and showed degree of improvement (index of therapeutic effect) of 60%~89%.

Improved was defined as the patients having skin rash to some extent subsided, symptoms such as itchy feeling to some extent alleviated, and the index of therapeutic effect was 20%~59%.

No effect was defined as the patients having no change or very little subsidence of skin rash, or rash aggravated, symptoms such as itchy feeling similar to that before treatment or aggravated, and the index of therapeutic effect was less than 20%.

The effective rate was calculated as follows:

$$\text{Effective Rate} = \frac{\text{No. of Cases Basically Cured} + \text{No. of Cases Obviously Effective}}{\text{Total No. of Cases in The Group}} \times 100\%$$

$$\text{Cure Rate} = \frac{\text{Number of Cases Basically Cured}}{\text{Total Number of Cases In the Group}} \times 100\%$$

3.10 Adverse Side Effect

Emphasis was placed on the observation of adverse side effects during treatment, including irritating symptoms, allergic symptoms, body absorption symptoms, and signs. Adverse side effects were classified into three degrees, Light, Moderate and Severe degree, according to the severity of symptoms.

3.11 Statistical Analysis of Trial

Clinical data of all eligible cases after careful examination, were statistically evaluated by computer using the corresponding statistical methods in accordance with the quality and distribution of data. Student's t-test, rank sum test, and Mann-Whitney U-test were used to evaluate the significance of differences between two means of data measurement. Chi-square test was used in enumeration data. Ridit analysis was used in rank group data.

Example 17.2. Phase III Clinical Trial.

The aim and clinical trial design of the phase III clinical trial is basically the same as that of the phase II clinical trial as indicated in Example 17. 1, supra. In phase III clinical trial, 200 patients of the total 400 cases were investigated as randomly double-blind and parallel method, another 200 patients were selected for an open trial.

Results of Phase II/III Clinical Trials:
1. The distribution of psoriasis types and stages patients in phase II/III clinical trials is listed in Table 18:

TABLE 18

Distribution of Psoriasis Type/Stage in Phase II/III Trials

| Group | No. of Cases | Psoriasis Vulgaris | | | | Stage | |
|---|---|---|---|---|---|---|---|
| | | Guttate Shape | Small Coin Shape | Plaque Shape | Mixed Shape | Progressive Stage | Resting Stage |
| Trial Phase II/III | | | | | | | |
| Treatment Group | 202 | 38 | 92 | 41 | 31 | 139 | 63 |
| Control Group | 221 | 52 | 91 | 43 | 35 | 136 | 85 |
| Statistical Analysis | | $\chi^2 = 1.62$, P > 0.05 | | | | $\chi^2 = 2.46$, P > 0.05 | |
| Open Group (Phase III) | 210 | 36 | 91 | 51 | 32 | 124 | 86 |

2. The degrees of severity for psoriasis patients in phase II/III clinical trials is listed in Table 19:

TABLE 19

Degrees of Severity for Psoriasis Patients in Phase II/III Trials.

| | 0 | 1 | 2 | 3 | 4 |
|---|---|---|---|---|---|
| Maximum diameter of skin lesion | nil | 1 cm–2 cm | 2.1 cm–4 cm | 4.1 cm–6 cm | 6.1 cm–8 cm |
| Red Plaque | nil | Dark red | Slightly red | Lightly colored | Bright red |
| Infiltration hypertrophy | nil | Bit raised above surrounding skin, not obvious by outward looking | raised above surrounding skin Comparatively obvious Moderate infiltration | raised above surrounding skin, obvious, hypertrophic | Severely hypertrophic, or leathery |
| Scales | nil | Bit by outward looking, thin, not obvious | Obvious outward looking, thin | Very obvious outward looking, more in form of flakes | Very thick, compiled, Dropped off when taking off clothes |
| Itching | nil | Slight itching, scratching less than three times a day | Moderate itching, scratching 4–6 times a day | Severe itching, Scratching 7–10 times a day | Serious degree of itching, practically continuous scratching |

3. The distribution of patients' scores before treatment in phase II/III clinical trials is listed in Table 20:

TABLE 20

Distribution of Patients' Score before Treatment in Phase II/III Trials

| Group | No. of Cases | Score before Treatment | | | | | |
|---|---|---|---|---|---|---|---|
| | | Diameter of Target Skin Lesion | Red Plaque | Hypertrophic Infiltration | Scale | Itch | Total Score |
| Trial Phase II/III | | | | | | | |
| Treatment Group | | | | | | | |
| Mean ± Deviation | 202 | 2.06 ± 1.03 | 2.86 ± 0.89 | 2.32 ± 0.81 | 2.41 ± 0.84 | 1.86 ± 0.91 | 11.5 ± 3.06 |
| Median | 202 | 2.0 | 3.0 | 2.0 | 2.0 | 2.0 | 11.0 |
| Range | 202 | 1–4 | 1–4 | 0–4 | 1–4 | 0–4 | 5–20 |

TABLE 20-continued

Distribution of Patients' Score before Treatment in Phase II/III Trials

| | | Score before Treatment | | | | | |
|---|---|---|---|---|---|---|---|
| Group | No. of Cases | Diameter of Target Skin Lesion | Red Plaque | Hypertrophic Infiltration | Scale | Itch | Total Score |
| Control Group | | | | | | | |
| Mean ± Deviation | 221 | 2.00 ± 1.00 | 2.81 ± 0.87 | 2.35 ± 0.87 | 2.47 ± 0.79 | 1.38 ± 1.01 | 11.5 ± 3.13 |
| Median | 221 | 2.0 | 3.0 | 2.0 | 2.0 | 2.0 | 12.0 |
| Range | 221 | 1–4 | 1–4 | 0–4 | 0–4 | 0–4 | 3–19 |
| Mann-Whitney Test* | | 0.56 (NS) | 0.55 (NS) | 0.29 (NS) | 0.82 (NS) | 0.09 (NS) | 0.14 (NS) |
| Open Group Phase III | | | | | | | |
| Mean ± Deviation | 210 | 2.01 ± 1.04 | 2.75 ± 0.84 | 2.28 ± 0.84 | 2.39 ± 0.74 | 1.75 ± 0.97 | 11.2 ± 3.02 |
| Median | 210 | 2.0 | 3.0 | 2.0 | 2.0 | 2.0 | 11.0 |
| Range | 210 | 1–4 | 1–4 | 0–4 | 1–4 | 0–4 | 4–20 |

*Non-parameter statistic of treatment/control groups with Z value. In parentheses, NS: P > 0.05.

4. The comparison of patients' score between treatment and placebo groups after six-week treatment is indicated in Table 21:

TABLE 21

Comparison of Patients' Score after Six Weeks Treatment in Phase II/III Trials

| | | Scores | | | | | |
|---|---|---|---|---|---|---|---|
| Group | No. of Cases | Diameter of Target Skin Lesion(cm) | Red Plaque | Hypertrophic Infiltration | Scale | Itch | Total Score |
| Trial Phase II/III | | | | | | | |
| Treatment Group | | | | | | | |
| Mean ± Deviation | 202 | 1.54 ± 1.04 | 1.51 ± 1.13 | 1.10 ± 1.00 | 0.79 ± 0.91 | 0.54 ± 0.83 | 5.49 ± 4.02 |
| Median | 202 | 1.0 | 1.0 | 1.0 | 1.0 | 0.0 | 5.0 |
| Range | 202 | 0–4 | 0–4 | 0–4 | 0–4 | 0–4 | 0–18 |
| Control Group | | | | | | | |
| Mean ± Deviation | 221 | 1.84 ± 1.00 | 2.11 ± 0.96 | 1.67 ± 0.94 | 1.22 ± 0.97 | 1.12 ± 0.96 | 7.96 ± 3.60 |
| Median | 221 | 2.0 | 2.0 | 2.0 | 1.0 | 1.0 | 8.0 |
| Range | 221 | 0–4 | 0–4 | 0–4 | 0–4 | 0–4 | 0–17 |
| Mann-Whitney Test* | | 2.96 () | 5.95 () | 5.76 () | 4.79 () | 6.77 () | 6.43 () |
| Open Group (Phase III) | | | | | | | |
| Mean ± Deviation | 210 | 1.46 ± 1.02 | 1.35 ± 0.89 | 0.90 ± 0.85 | 0.56 ± 0.74 | 0.40 ± 0.71 | 4.68 ± 3.32 |
| Median | 210 | 1.0 | 1.0 | 1.0 | 0.0 | 0.0 | 4.0 |
| Range | 210 | 0–4 | 0–4 | 0–4 | 0–3 | 0–4 | 0–16 |

*Non-parameter statistic of treatment/control groups with Z value. In parentheses, **: P < 0.01.

5. The changes of patients' scores after six-week treatment is listed in Table 22:

TABLE 22

Changes of Patients' Score after Six Weeks Treatment in Phase I/III Trials

| Group | No. of Cases | Changes of Scores | | | | | |
|---|---|---|---|---|---|---|---|
| | | Diameter of Target Skin Lesion (cm) | Red Plaque | Hypertrophic Infiltration | Scale | Itch | Total Score |
| Trial Phase II/III | | | | | | | |
| Treatment Group | | | | | | | |
| Mean ± Deviation | 202 | 0.52 ± 0.95 | 1.34 ± 1.16 | 1.22 ± 0.97 | 1.61 ± 1.07 | 1.32 ± 0.99 | 6.02 ± 3.95 |
| Median | 202 | 0 | 1.0 | 1.0 | 2.0 | 1.0 | 6.0 |
| Range | 202 | −2–4 | −2–4 | −1–3 | −1–4 | −1–4 | −2–16 |
| Control Group | | | | | | | |
| Mean ± Deviation | 221 | 0.16 ± 0.65 | 0.70 ± 0.93 | 0.67 ± 0.85 | 1.25 ± 1.02 | 0.76 ± 1.01 | 3.55 ± 3.23 |
| Median | 221 | 0 | 1.0 | 0 | 1.0 | 1.0 | 3.0 |
| Range | 221 | −2–3 | −2–4 | −2–3 | −2–4 | −2–4 | −9–13 |
| Mann-Whitney Test* | | 4.62 () | 5.91 () | 5.85 () | 3.46 () | 5.71 () | 6.47 () |
| Open Group (Phase III) | | | | | | | |
| Mean ± Deviation | 210 | 0.55 ± 0.85 | 1.40 ± 1.04 | 1.37 ± 0.92 | 1.83 ± 0.92 | 1.35 ± 1.03 | 6.50 ± 3.35 |
| Median | 210 | 0 | 1.5 | 1.0 | 2.0 | 1.0 | 6.0 |
| Range | 210 | −1–4 | −3–4 | −1–4 | 0–4 | −1–4 | −5–14 |

*Non-parameter statistic of treatment/control groups with Z value.
**P < 0.01.

6. The comprehensive effects after six-week treatment is demonstrated in Table 23:

TABLE 23

Comprehensive Effects after Six-Week Treatment in Phase II/III Trials

| | No. of Cases | No-effect | Effective | Obviously Effective | Basically Cured | Cure Rate (%) | P* Value | Effective (%) | P* Value |
|---|---|---|---|---|---|---|---|---|---|
| Trial Phase II/III | | | | | | | | | |
| Treatment Group | 202 | 41 | 62 | 68 | 31 | 15.3 | <0.001 | 49.0 | <0.001 |
| Control Group | 221 | 83 | 105 | 27 | 6 | 2.7 | | 14.9 | |
| Open Group (Phase III) | 210 | 20 | 77 | 86 | 27 | 12.9 | — | 53.8 | — |

*Chi-Square test.

7. Summary of the results after different weeks of treatment

Table 24 showed the comparison of the patients' scores after different weeks of treatment. Improvement had been shown progressively during the six-week treatment, which was statistically significant.

TABLE 24

Comparison of Score and Change of Score in Different Weeks after Treatment between Treatment Group and Control Group during Clinical Trial Phase II/III*

| | Diameter of Target Skin Lesion (cm) | Red Plaque | Hypertrophic Infiltration | Scale | Itch | Total Score |
|---|---|---|---|---|---|---|
| One Week after Treatment | | | | | | |
| Score | NS | NS | P < 0.05 | NS | NS | NS |
| Change of Score | NS | P < 0.05 | P < 0.01 | NS | P < 0.01 | P < 0.01 |

TABLE 24-continued

Comparison of Score and Change of Score in Different Weeks after Treatment between Treatment Group and Control Group during Clinical Trial Phase II/III*

|  | Diameter of Target Skin Lesion (cm) | Red Plaque | Hypertrophic Infiltration | Scale | Itch | Total Score |
|---|---|---|---|---|---|---|
| Two Weeks after Treatment | | | | | | |
| Score | NS | NS | P < 0.01 | P < 0.05 | P < 0.01 | P < 0.01 |
| Change of Score | NS | P < 0.01 | P < 0.001 | NS | P < 0.001 | P < 0.001 |
| Three Weeks after Treatment | | | | | | |
| Score | NS | P < 0.001 | P < 0.001 | P < 0.001 | P < 0.001 | P < 0.001 |
| Change of Score | P < 0.01 | P < 0.001 | P < 0.001 | P < 0.01 | P < 0.001 | P < 0.001 |
| Four Weeks after Treatment | | | | | | |
| Score | NS | P < 0.001 | P < 0.001 | P < 0.001 | P < 0.001 | P < 0.001 |
| Change of Score | P < 0.001 | P < 0.001 | P < 0.001 | P < 0.01 | P < 0.001 | P < 0.001 |
| Five Weeks after Treatment | | | | | | |
| Score | P < 0.05 | P < 0.001 | P < 0.001 | P < 0.001 | P < 0.001 | P < 0.001 |
| Change of Score | P < 0.001 | P < 0.001 | P < 0.001 | P < 0.01 | P < 0.001 | P < 0.001 |
| Six Weeks after Treatment | | | | | | |
| Score | P < 0.01 | P < 0.001 | P < 0.001 | P < 0.001 | P < 0.001 | P < 0.001 |
| Change of Score | P < 0.001 | P < 0.001 | P < 0.001 | P < 0.01 | P < 0.001 | P < 0.001 |

*Non-parameter statistics of treatment/control groups with Z value, all of scores in treatment group are lower than those in control group, and changes of score in treatment group are higher than those in control group. NS: P > 0.05.

The results of the therapeutic efficacies with the cure rate, the effective rate, the progression of the disease, and symptoms of skin lesion are shown in the following Tables 25, 26, and 27. The topical preparation of the present invention showed effective treatment results on the treatment group patients.

TABLE 25

Comparison of Comprehensive Effects in Different Weeks after Treatment between Treatment Group and Control Group in Phase II/III Trials

|  | Basically Cured Rate (%) | | | Total Effective Rate (%) | | |
|---|---|---|---|---|---|---|
|  | Treatment Group | Control Group | P Value | Treatment Group | Control Group | P Value |
| Control Clinical Trial Phase II/III | | | | | | |
| One Week after Treatment | 0.0 | 0.0 | — | 2.5 | 0.0 | <0.05 |
| Two Weeks after Treatment | 0.5 | 0.0 | 0.48 | 7.9 | 0.5 | <0.001 |
| Three Weeks after Treatment | 1.5 | 0.5 | 0.35 | 12.9 | 3.2 | <0.001 |
| Four Weeks after Treatment | 2.0 | 0.5 | 0.20 | 28.2 | 6.3 | <0.001 |
| Five Weeks after Treatment | 5.9 | 0.9 | <0.01 | 41.1 | 12.2 | <0.001 |
| Six Weeks after Treatment | 15.3 | 2.7 | <0.001 | 49.0 | 14.9 | <0.001 |
| Open Clinical Trial Phase III | | | | | | |
| One Week after Treatment | 0.0 | — | — | 0.5 | — | — |
| Two Weeks after Treatment | 1.4 | — | — | 4.8 | — | — |
| Three Weeks after Treatment | 3.8 | — | — | 11.9 | — | — |
| Four Weeks after Treatment | 4.8 | — | — | 24.3 | — | — |
| Five Weeks after Treatment | 6.2 | — | — | 38.1 | — | — |
| Six Weeks after Treatment | 12.9 | — | — | 53.8 | — | — |

*Chi-square test or Fisher's exact test.

TABLE 26

Comprehensive Effects of Treatment Group in Different Stage during Clinical Trial Phase II/III

| Clinical Stage | No. of Cases | No-effect | Effective | Obviously Effective | Basically Cured | Cure Rate (%) | P* Value | Effective (%) | P* Value |
|---|---|---|---|---|---|---|---|---|---|
| Clinical Treatment Group Phase II/III | | | | | | | | | |
| Progressive Stage | 139 | 28 | 42 | 44 | 25 | 18.0 | 0.12 | 49.6 | 0.79 |
| Resting Stage | 63 | 13 | 20 | 24 | 6 | 9.5 | | 47.6 | |
| Open Group Phase III | | | | | | | | | |
| Progressive Stage | 124 | 13 | 45 | 47 | 19 | 15.3 | 0.20 | 53.2 | 0.84 |
| Resting Stage | 86 | 7 | 32 | 39 | 8 | 9.3 | | 54.7 | |

*Chi-square test.

TABLE 27

Comprehensive Effects of Treatment Group in Patients with Different Skin Lesion in Phase II/III (after Six-Week Treatment)

| Type of Skin Lesion | No. of Cases | No-effect | Effective | Obviously Effective | Basically Cured | Cure Rate (%) | P* Value | Effective (%) | P* Value |
|---|---|---|---|---|---|---|---|---|---|
| Clinical Treatment Group Phase III | | | | | | | | | |
| Guttate Shape | 38 | 6 | 8 | 16 | 8 | 21.1 | 0.34 | 63.2 | 0.27 |
| Coin Shape | 92 | 22 | 29 | 30 | 11 | 12.0 | | 44.6 | |
| Small Plaque Shape | 41 | 8 | 13 | 15 | 5 | 12.2 | | 48.8 | |
| Mixed Shape | 31 | 5 | 12 | 7 | 7 | 22.6 | | 45.2 | |
| Open Group Phase III | | | | | | | | | |
| Guttate Shape | 36 | 4 | 10 | 16 | 6 | 16.7 | 0.85 | 61.1 | 0.34 |
| Coin Shape | 91 | 9 | 39 | 33 | 10 | 11.0 | | 47.3 | |
| Small Plaque Shape | 51 | 3 | 17 | 24 | 7 | 13.7 | | 60.8 | |
| Mixed Shape | 32 | 4 | 11 | 13 | 4 | 12.5 | | 53.1 | |

*Chi-square test.

8. Adverse side effects

During the clinical trials phase II and phase III, the patients were examined and recorded for adverse effects. Table 28 indicates the statistics of adverse effects among the treatment groups during the clinical trials. Table 29 indicates the laboratory test results of different indexes in different patient groups during the clinical trials. Table 30 records the reasons for withdrawal of the patients in the treatment groups. It has shown that the treatment of the topical preparation of the present invention does not cause significant adverse effects in the patients.

TABLE 28

Adverse Reaction in Different Patient Groups during Phase II/III Trials

| Adverse Reaction | Treatment Group (n = 204) | Control Group (n = 226) | P* Value | Open Group (n = 216) |
|---|---|---|---|---|
| Clinical Appearance | | | | |
| Red Patch | 7 | 7 | 0.94 | 3 |
| Blister | 0 | 0 | — | |
| Erosion | 0 | 1 | 1.00 | 1 |
| Pain | 3 | 3 | 1.00 | 4 |
| Itching | 1 | 1 | 1.00 | 2 |
| Edema | 1 | 3 | 0.63 | 3 |
| Others | 0 | 0 | — | 1 |
| Severity | | | | |
| Mild | 7 | 6 | 0.63 | 6 |
| Moderate | 3 | 7 | 0.34 | 3 |
| Serious | 2 | 2 | 1.00 | 5 |
| Total | 12 | 15 | 0.75 | 14 |
| Percentage (%) | 5.9 | 6.6 | — | 6.5 |

*Fisher's exact test.

TABLE 29

Laboratory Test Results in Different Patient Groups during Phase II/III Trials*

| Laboratory Test | Treatment Group (197)*** | Control Group (215)*** | P** Value | Open Group (207)*** |
|---|---|---|---|---|
| Hemoglobin | 0 | 0 | — | 0 |
| Red Blood Cell | 0 | 0 | — | 0 |
| White Blood Cell | 0 | 1 | 1.00 | 0 |

TABLE 29-continued

Laboratory Test Results in Different Patient Groups during Phase II/III Trials*

| Laboratory Test | Treatment Group (197)*** | Control Group (215)*** | P** Value | Open Group (207)*** |
|---|---|---|---|---|
| Platelet | 0 | 1 | 1.00 | 1 |
| ALT | 0 | 0 | — | 0 |
| BUN | 0 | 1 | 1.00 | 1 |
| HCG | 0 | 0 | — | 0 |
| Urine Sugar | 0 | 0 | — | 0 |
| Urine Protein | 1 | 2 | 1.00 | 1 |
| Microscopic Exam | 5 | 3 | 0.49 | 0 |
| Total | 6 | 8 | 0.92 | 3 |

*Normal before treatment but abnormal after treatment.
**Result of comparison between treatment group and control group with Fisher's exact test.
***5 patients in treatment group, 6 patients in control group and 3 patients in open group did not participate laboratory test.

TABLE 30

Analysis of Withdrawal Reason in Different Patient Groups during Clinical Trial Phase II/III

| Reason for Withdrawal | Treatment Group | Control Group | Open Group |
|---|---|---|---|
| Lost Follow up | 3 | 2 | 7 |
| No Effect | 0 | 4 | 4 |
| Patient Not Cooperate | 0 | 0 | 1 |
| Adverse Reaction | 3 | 7 | 8 |
| Changed to Other Scheme | 0 | 0 | 1 |
| Statistics Test | $\chi^2 = 3.73, P > 0.05$ | | — |
| Total | 6 | 13 | 21 |

Conclusion:

The phase II and phase III clinical trials showed that the topical preparation of the present invention containing anti-human-IL-8 antibodies was effective in topical treatment of psoriasis vulgaris. As indicated in research data, the IL-8 MAb in the topical preparation of present invention possesses anti-human IL-8 effects which could inhibit leukocyte chemotaxis, and anti-inflammatory action which could modulate the abnormal proliferation and differentiation of keratinocyte.

EXAMPLE 18

Preparation of Anti-human IL-8 Chimeric Antibody

The chimeric antibody to human IL-8 of the present invention can be prepared as following:

1. Preparation of cDNA Libraries (a) Source of mRNA: The mouse hybridoma cell line#18-60, which secrets anti-human IL-8 monoclonal antibody, can be used as the source of mRNA.

(b) mRNA purification: mRNA can be isolated from hybridoma using commercial reagents (e.g., QuickPrep mRNA Purification Kit. Amersham Pharmacia Biotech Cat No. 27-9254-01)

(c) First-strand cDNA synthesis: The first-strand cDNA can be synthesized from mRNA primed with Random Hexamers using reverse transcriptase.

(d) Primary PCR: The DNA fragment encoding variable heavy (VH) and light (VL) chains of antibody can be amplified in two separate reactions. The primers can be designed specially or using Ig-Primer set (Novagen, Cat No. 69831-3).

(e) Purification of primary PCR product: The amplified VH- and VL-chain fragments can be purified separately by agarose gel electrophoresis to remove primers and extraneous amplification products, using the MicroSpin Columns (Bio 101 System, Q.BIOgene Cat #1101-200).

(f) Gel quantitation of primary PCR products: The purified VH- and VL-chain DNA products can be quantitated on an agarose gel alongside a DNA marker of known concentration. The quantity of VH- and VL-chains can be determined and the relative quantity ratio of VH-chain to VL-chain can be calculated so that the optimal amount of each can be added to the assembly reaction.

(g) Assembly of the VH- and VL-chains: The purified VH- and VL-chain cDNA products can be assembled into a single chain fragment (ScFv) using a oligomer linker, e.g., $(Gly_4Ser)_3$.

(h) Second PCR amplification reaction: The assembled antibody ScFv DNA fragment can be amplified with the introduction of restriction site for cloning into the pCANTAB $5^E$ vector (Pharmacia Cat#27-9400-01). SfiI and NotI site are added to the 5'- and 3'-ends of the ScFv fragment, respectively.

(i) Purification of amplified $2^{nd}$ PCR and gel quantitation: Gel electrophoresis and BIO 101 system can be used for this purification (see also step (e) above) to remove unincorporated linker oligomer and dNTPs. The purified ScFv fragment can be quantitated on an agarose gel.

(j) Ligation to the vector and transformation into E. coli HB2151: The ScFv fragment can be sequentially digested using restriction enzymes at the SfiI and NotI sites to generate cohesive ends for ligation to the vector, e.g. the pCANTAB $5^E$ vector (Pharmacia Cat#27-9400-01). The recombinant vector can be transformed into E. coli HB2151 to obtain the recombinant library. Alternatively, purified VH or VL can be amplified independently, and ligation to the vector, transformation into E. Coli HB2151 to obtain VH and VL cDNA library for colony lift assay or phage display selection.

2. Selection of Functional ScFv Fragment

Colony Lift Assay can be used for the selection of functional ScFv fragment. Alternatively, "Phage Display-Panning" (Pharmacia Biotech Manual) can also be used for this purpose.

Colony Lift Assay: Transformed E. coli HB2151 cells obtained from (1)(j) can be poured into 2XYT plates with Amp and glucose. The plates can be incubated at 37° C. overnight to obtain approximately 300 well-isolated colonies per plate.

For each plate, all colonies can be lifted onto a dry nitrocellulose membrane that can be placed, colony-side up, on top of a 2XYT plate with Amp and IPTG. The plates together with the membranes can be incubated for 3 hours. The original plates can be returned to the incubator.

After incubation, the nitrocellulose membranes can be lifted from the plates; washed with TNT buffer a few times to remove all the colonies; blocked with 4% NFDM; probed with anti-Etag in blocking buffer at 4° C. overnight; probed with anti-mouse HRP; and developed in the dark with shaking in 4-CN solution for approximately 40 minutes for color reaction.

Colonies showing color reaction on the nitrocellulose membranes can be individually picked up from the corresponding positions on the original plates; placed individually into a cultural tube with 2XYT-AG medium; and incubated overnight with shaking at 37° C. The bacteria in the cultural tubes can be spun down and resuspended in 2XYT-AI medium and incubated at 37° C. for 3 hours. The bacteria will then be spun down and extracted with TES buffer to yield the periplasmic (ScFv) extraction.

The presence of ScFv in the periplasmic extractions can be tested by first separating proteins in the extracts using SDS-PAGE and detecting ScFv using the Western blot. The antigen binding affinity of ScFv can be tested by ELISA. Bacteria cultures containing the functional ScFv fragment can then be identified and selected.

Primers, including the enzyme sites, for the VH and VL fragment can be designed and synthesized. Plasmids containing the functional VH and VL can be purified and then amplified using PCR. The amplified functional VH and VL fragment products can be identified by sequencing.

3. Construction of the Expression Vector Encoding the Chimeric Antibody

Standard ligation techniques can be used for construction of suitable vectors containing the selected VH and VL encoding and control sequences. Isolated plasmids or DNA fragments can be cleaved, tailored, and religated in the form of required plasmids. The methods employed are not dependent on the DNA source, or intended host.

Cleavage can be performed using restriction enzyme (or enzymes) in suitable buffer. In general, about 1 μg of plasmid or DNA fragments can be used with about 1 unit of enzyme in about 20 μl of buffer solution. Information regarding the amounts of appropriate buffers and substrate for a particular restriction enzyme is usually provided by the manufacturer. In normal circumstances, an incubation time of about 1 hour at 37° C. is optimal. After the incubation, protein can be removed by extraction with phenol and chloroform, and the nucleic acid can be recovered from the aqueous fraction by precipitation with ethanol.

If blunt ends are required, the preparation can be treated for 15 minutes at 15° C. with about 10 units of E. coli DNA Polymerase I (Klenow), followed by phenol-chloroform extraction, and ethanol precipitation. Size separation of the cleaved fragments can be performed by agarose gel electrophoresis.

For ligation, approximately equimolor amounts of the desired components, suitably end tailored to provide correct matching, can be treated with T4 DNA ligase. When cleaved vectors are used as components, it may be useful to prevent religation of the cleaved vector by pretreatment with bacterial alkaline phosphatase. Correct ligations for plasmid construction can be confirmed by transfecting E. coli. HB101 with the ligation mixture. Successful transformants can be selected by antibiotics properly. Plasmids from the transformants can then be prepared, analyzed by restriction digestion and/or sequencing.

The preferred vectors used in this example are vectors αLys-30 and αLys-17, which can be paired with the functional VH and VL fragment obtained from (2) to form the VH and VL expression vectors for the experimental expression of the chimeric antibody.

(a) Construction of VH-αLys-30 vector: The αLys-30 vector, containing Human Ig γ1, can be paired with the functional VH gene obtained in (2) to form the VH expression vector. The αLys-30 vector DNA can be prepared by conventional method(s). The αLys-30 vector DNA and the VH DNA can be suitably end-tailored by enzyme cleavage in suitable buffer at 37° C. for about 1 hour, using restriction enzyme(s). The resultant DNA components can be ligated by treatment with T4 DNA ligase and correct ligation can be confirmed b transformation the vector into E. coli HB101. Successful transformation can be selected by ampicillin or other proper antibiotics. Plasmids from the successful transformants will then be prepared and analyzed by restriction digestion and/or sequencing.

(b) Construction of VL-αLys-17 vector: The αLys-17 vector, containing Human Ig κ, can be paired with the functional VL gene obtained in (2) to form the VL expression vector. The αLys-17 vector DNA can be prepared by conventional method(s). The αLys-17 vector DNA and the VL DNA can be suitably end-tailored by enzyme cleavage in suitable buffer at 37° C. for about 1 hour, using restriction enzyme(s). The resultant DNA components can be ligated by treatment T4 DNA ligase and correct ligation can be confirmed by transformation the vector into E. coli HB101. Successful transformation can be selected by ampicillin or other proper antibiotics. Plasmids from the successful transformants will then be prepared; analyzed by restriction digestion; purified; verified by gel electrophoresis; and confirmed by sequencing 4. Expression and Characterization of the Chimeric Antibody Myeloma cell line SP2/0 (but not limited to) which does not produce endogenous immunoglobulin can be used as the expression host cell. The cell line can be cultured in RPMI 1640 with 10% FCS under 5% $CO_2$ to maintain good cell growth and morphology.

The SP2/0 can be transfected with the VH-αLys-30 and VL-αLys-17 plasmids obtained from (3). Several methods can be used for transfection (e.g., electrode poration and lipofection reagent). Positive expression clones can be selected by incubating the SP2/0 cells in cultural medium containing appropriate amounts of hydromycin, mycophenolic acid and xanthine; and screening the supernatant from growing cell clone/foci using ELISA. The cell clones, whose supernatant were giving the strong reaction in ELISA can be subcloned. The subcloned cells may be stored in liquid nitrogen.

The chimeric antibodies produced by the host cells can be collected using techniques, such as affinity chromatography using target antigen or protein A/G column. The immunoreactivity and neutralizing activity of the collected chimeric antibodies can be characterized by a series of experiments. For immunoreactivity, Eptope Recognition (as described in Example 4); Western blot (as described in Example 2-3); and specificity test (as described in Example 2-2) can be carried out. For neutralizing activity, the monoclonal antibody neutralizing test, as described in Example 3, can be carried out.

While the invention has been described by way of examples and in terms of the preferred embodiments, it is to be understood that the invention is not limited to the disclosed embodiments. On the contrary, it is intended to cover various modifications as would be apparent to those skilled in the art. Therefore, the scope of the appended claims should be accorded the broadest interpretation so as to encompass all such modifications.

I claim:

1. A topical preparation comprising
an antibody to human interleukin-8 (IL-8) and a pharmaceutically acceptable carrier for treatment of patients with skin inflammatory disease;
wherein said antibody is a monoclonal antibody;
wherein said monoclonal antibody in said topical preparation is a murine anti-human IL-8 monoclonal antibody;

wherein said murine anti-human IL-8 monoclonal antibody is produced by a hybridoma; and wherein said hybridoma is selected from the group consisting of I8-60 (ATCC accession No. CRL-12528), I8-S2 (ATCC accession No. CRL-12527), and 3C6 (ATCC accession No. CRL-12529).

2. The topical preparation according to claim 1, wherein the skin inflammatory disease is psoriasis or eczema.

3. The topical preparation according to claim 1, wherein the pharmaceutically acceptable carrier for topical treatment is selected from the group consisting of neutral sterile cream, base cream, gel, jelly, ointment, aerosol, patch, and powders.

4. The topical preparation according to claim 1, wherein said pharmaceutical acceptable carrier is a base cream.

5. The topical preparation according to claim 4, wherein said antibody is no more than about 100 µg per g of said base cream.

6. The topical preparation according to claim 4, wherein the base cream comprises an emulsifying agent, an oil-phase ingredient, and a water-phase ingredient.

7. The topical preparation according to claim 6, wherein the emulsifying agent is fatty alcohol polyoxyethylene (20) ether, polyoxyl (6) stearate, or a combination thereof.

8. The topical preparation according to claim 6, wherein the oil-phase ingredient is selected from the group consisting of cetyl alcohol, stearyl alcohol, stearic acid, liquid paraffin, and dimethicone.

9. The topical preparation according to claim 6, wherein the water phase ingredient is selected from the group consisting of glycerol and ethyl paraben.

10. A method for preparing the topical preparation of claim 1 comprising obtaining antibody against human IL-8, and mixing said antibody against human IL-8 with said pharmaceutically acceptable carrier;

wherein said antibody is a monoclonal antibody;

wherein said monoclonal antibody in said topical preparation is a murine anti-human IL-8 monoclonal antibody;

wherein said murine anti-human IL-8 monoclonal antibody is produced by a hybridoma; and wherein said hybridoma is at least one selected from the group consisting of I8-60 (ATCC accession No. CRL-12528), I8-S2 (ATCC accession No. CRL-12527), and 3C6 (ATCC accession No. CRL-12529).

* * * * *